US006516294B1

(12) United States Patent
Norman

(10) Patent No.: US 6,516,294 B1
(45) Date of Patent: Feb. 4, 2003

(54) NUCLEAR RECEPTOR FOR 1α,25-DIHYDROXYVITAMIN $D_3$ USEFUL FOR SELECTION OF VITAMIN $D_3$ LIGANDS AND A METHOD THEREFOR

(75) Inventor: Anythony W. Norman, Riverside, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 09/346,070

(22) Filed: Jul. 1, 1999

(51) Int. Cl.⁷ .......................... G06F 9/455; G09B 23/26; C07C 401/00
(52) U.S. Cl. .............. 703/11; 703/2; 703/12; 702/27; 434/277; 434/278; 556/653
(58) Field of Search ................ 435/7.1, 7.93; 424/198.1; 436/501; 930/120; 514/167; 434/277, 278; 702/27; 552/653; 703/11, 12, 2

(56) References Cited

U.S. PATENT DOCUMENTS 5,883,294 A 3/1999 Scanlan et al. ............. 562/471

FOREIGN PATENT DOCUMENTS

| WO | WO/93/07290 | 4/1993 |
| WO | WO/97/21993 | 6/1997 |

OTHER PUBLICATIONS

Yamamoto et al. Conformationally restricted analogs of 1a–25–dihydroxyvitamin D3 and its 20–epimer: compounds for study of the three–dimensional structure of vitamin D responsible for binding to the receptor. J. Med. Chem, vol. 39, pp. 2727–2737, 1996.*

Liu et al. Differential interaction of 1a,25–dihydroxyvitamin D3 analogues and their 20–epi homologues with the vitamin D receptor. J. Biol. Chem., vol. 272, pp. 3336–3345, 1997.*

Andrzej M. Brzozowski et al., Molecular Basis of Agonism and Antagonism in the Oestrogen Receptor, *Nature*, 389:753–758, (Oct. 16, 1997).

Richard L. Wagner, et al. A Structural Role for Hormone in the Thyroid Hormone Receptor, *Nature*, 378:690–697 (Dec. 14, 1995).

\* cited by examiner

*Primary Examiner*—John S. Brusca
*Assistant Examiner*—Marjorie A. Moran
(74) *Attorney, Agent, or Firm*—Hana Verny

(57) ABSTRACT

The nuclear receptor for the steroid hormone 1α,25-dihydroxyvitamin $D_3$, its ligand binding domain, three-dimensional model thereof and a method for selection of suitable vitamin $D_3$ binding to the 1α,25-dihydroxyvitamin $D_3$ receptor. A three-dimensional model for residues 142–427 of the ligand binding domain of the human nuclear receptor for 1α,25-dihydroxyvitamin $D_3$ used to identify the interaction of the conformationally flexible natural hormone 1α,25(OH)$_2$D$_3$ and a number of related analogs with the receptor ligand binding domain. A method for identification and generation of new potential analog drug forms of dihydroxyvitamin $D_3$.

10 Claims, 10 Drawing Sheets

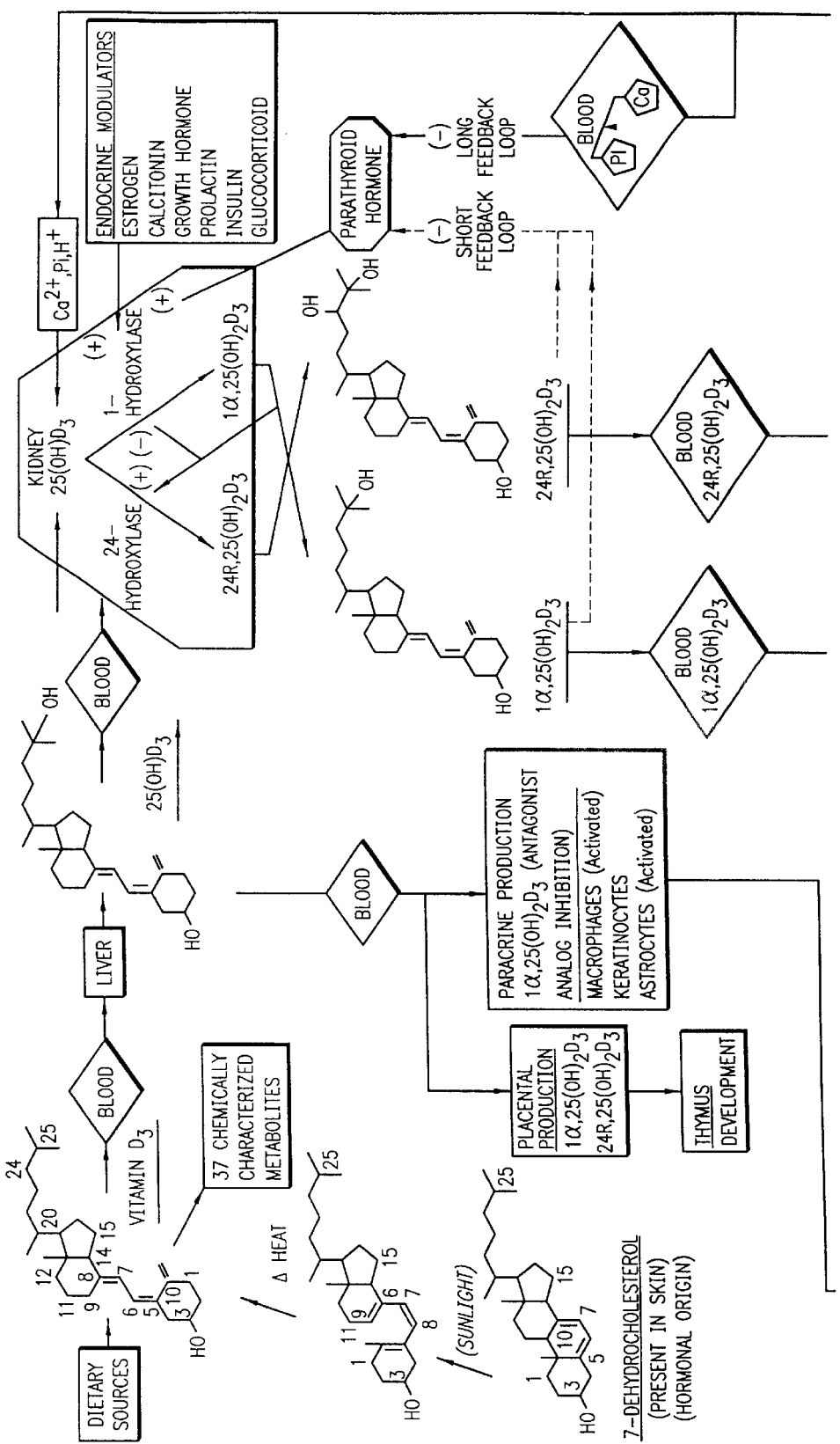
FIG. 1-A

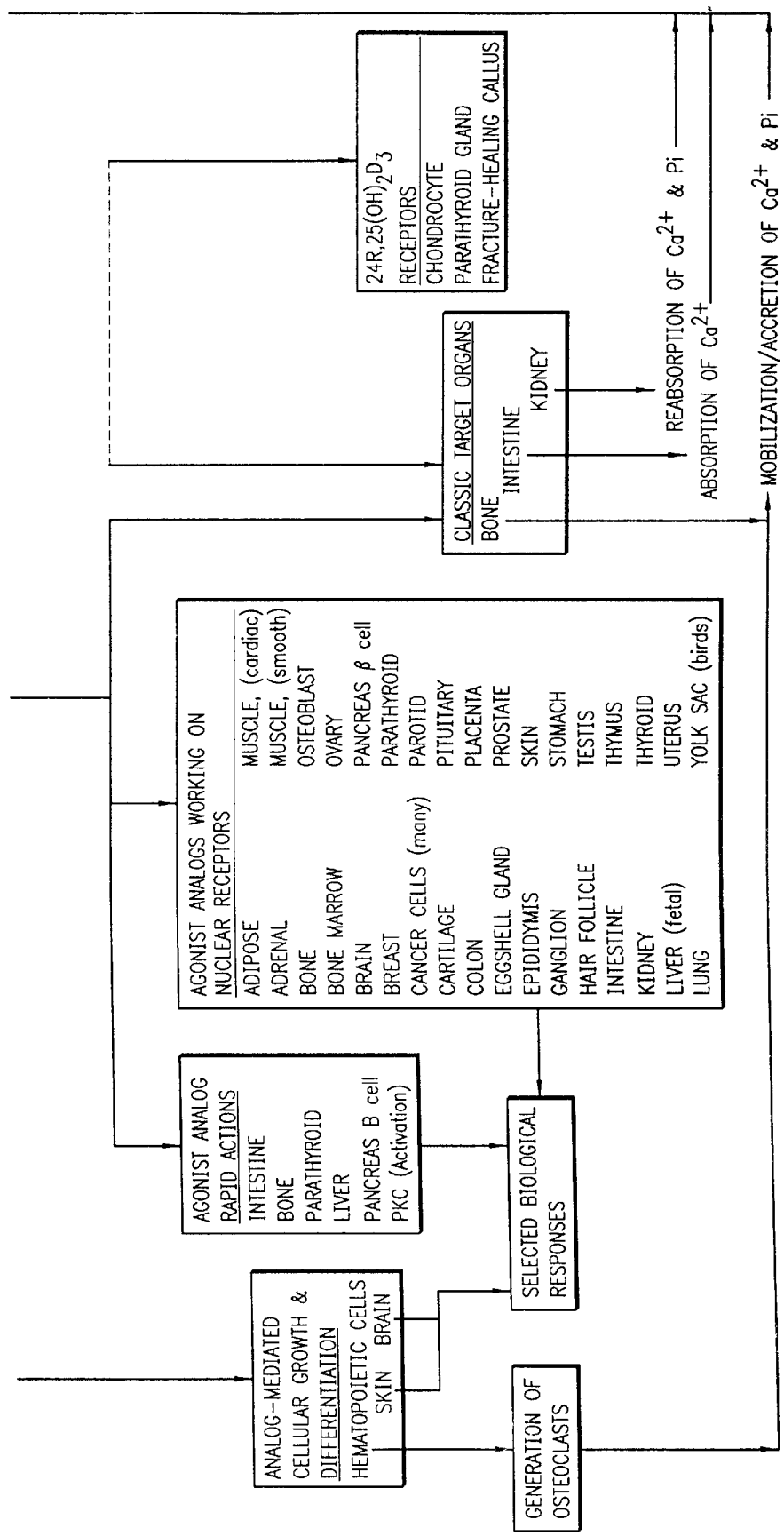
FIG. 1-B

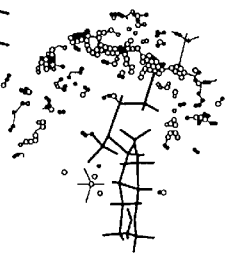
FIG. 2A-1
Top view (as shown in structure)
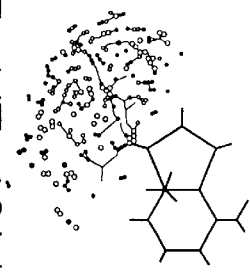
FIG. 2A-2
Top view (as shown in structure)
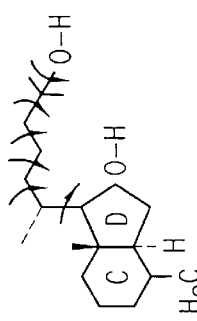
FIG. 2A-3
In-plane view
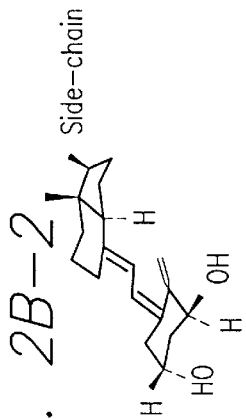
FIG. 2B-1
Side-chain
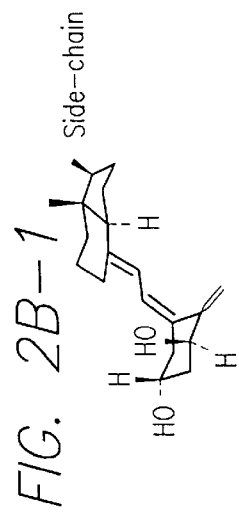
FIG. 2B-2
Side-chain
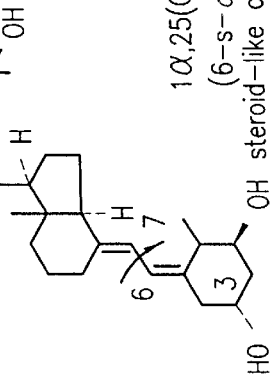
FIG. 2C-1
1α,25(OH)₂D₃
(6-s-cis or steroid-like conformation)
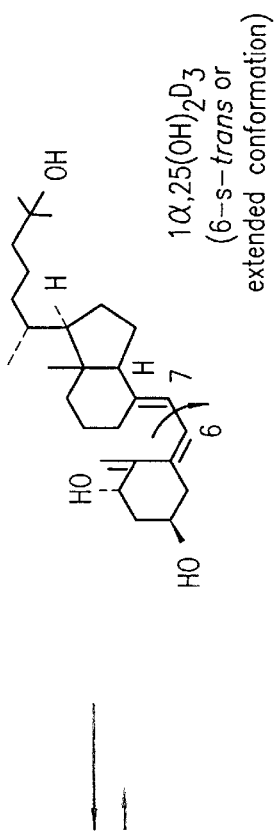
FIG. 2C-2
1α,25(OH)₂D₃
(6-s-trans or extended conformation)

```
VDR  140   HKTYDPTYSDFCQFRPPVRVNDGGGSHPSRPNSRHTPSFS
TR   157      RPEPTPEE DLIHVATEAHRSTNAQGS..H KQRRKFL
                      [    HX #1    ]              [HX#2]

<<<<VDR.loop >>>>>>>>
VDR  180   GDSSSSCSDHCITSSDMMDSSSFSNLDLSEEDSDDPSVTL
TR   193   PDDIGQSPIVSMPGDDKVD.....................

>>>>             ■■  ■
VDR  220   ELSQLSMLPHLADLVSYSIQKVIGFAKMIPGFRDLTSEDQ
TR   212   ....LEAFSEFTKIITPAITRVVDFAKKLPMFSELPCEDQ
                   [     HX #3     ]  [HX #4]  [HX #5/6]

■■   ■      ■            ■
VDR  260   IVLLKSSAIEVIMLRSNESFTMDDMS TCGNQDYKYRVSD
TR   248   IILLKGCCMEIMSLRAAVRYDPASDTLTLS.GEMAVK.RE
           [   HX #5/#6    ]                      [ ]

■■   ■
VDR  300   VTKAGHSLELIEPLIKFQVGLKKLNLHEEEHVLLMAICIV
TR   286   QLKNGGLGVVSDAIFELGKSLSAFNLDDTEVALLQAVLLM
           [HX#7]   [    HX #8    ]    [   HX #9   ]

VDR  340   SPDRPGVQDAALIEAIQDRLSNTLQTYIRCRHPPPGSHLL
TR   326   STDRSGLLCVDAIEKSQEAYLLAFEHYV..NHRKHNIPHF
              [         HX #10         ]        [ ]

■  ■■          ■
VDR  380   YAKMIQKLADLRSLNEEHSKQYRCLSFQ.PECSMKLTPLVL
TR   364   PKLLMKVTDLRMIGACHASRFLHMKVECPT.EL.FPPLFL
           [             HX #11           ]   [HX12]

■
VDR  420   EVFGNEIS    SEQ ID NO: 1
TR   403   EVFEDQEV    SEQ ID NO: 2
           [H12]
```

FIG. 5

FIG. 6B
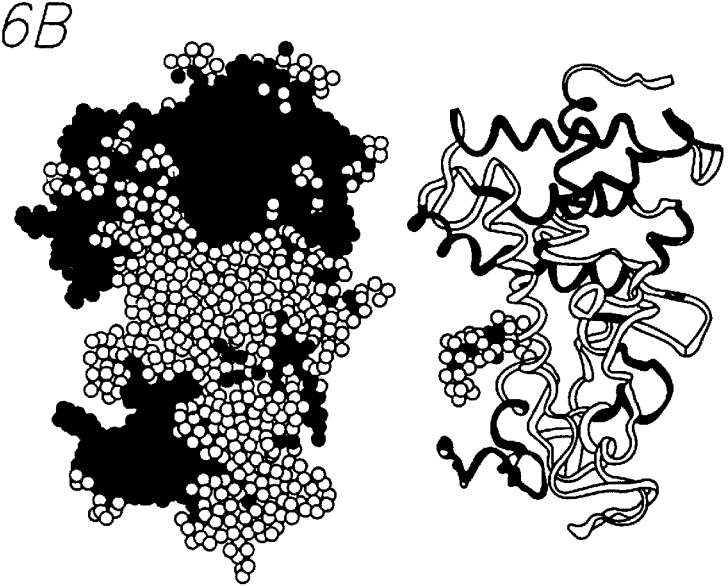
FIG. 6C
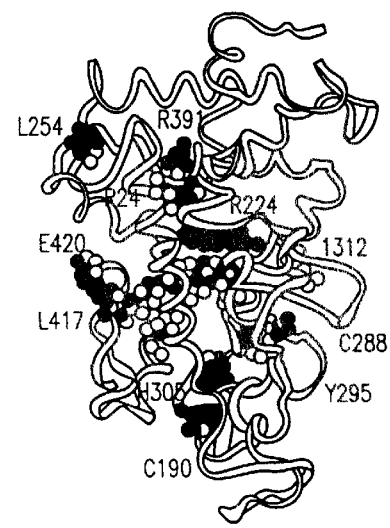
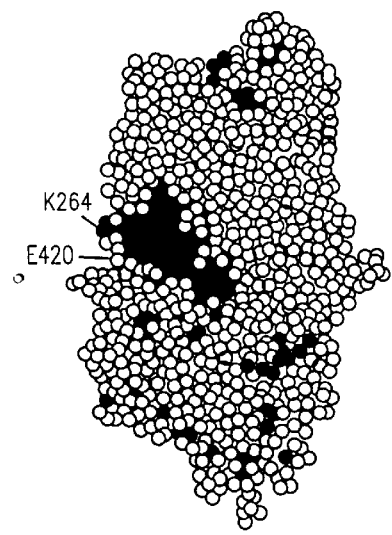
FIG. 6D

NUCLEAR RECEPTOR FOR 1α,25-DIHYDROXYVITAMIN D₃ USEFUL FOR SELECTION OF VITAMIN D₃ LIGANDS AND A METHOD THEREFOR

This invention was made with government support under Grant No. DK09012, awarded by the National Institute of Health. The government has certain rights in this invention.

BACKGROUND OF THE INVENTION

1. Field of Invention

This invention concerns the nuclear receptor for the steroid hormone 1α,25-dihydroxyvitamin $D_3$, its ligand binding domain three-dimensional model thereof and a method for selection of suitable vitamin $D_3$ binding to the 1α,25-dihydroxyvitamin $D_3$ receptor. In particular, the invention concerns a three-dimensional model for residues 142–427 of the ligand binding domain of the human nuclear receptor for 1α,25-dihydroxyvitamin $D_3$ used to identify the interaction of the conformationally flexible natural hormone 1α,25(OH)$_2$D$_3$ and a number of related analogs with the receptor ligand binding domain. The optimal orientation of the model provides a generally useful method for identification and generation of new potential analog drug forms of dihydroxyvitamin $D_3$.

2. Background Art and Related Disclosures

The receptors for all of the steroid hormones, such as 1α,25-dihydroxyvitamin $D_3$, thyroid hormone, retinoic acid, triodothyronine, estradiol, cortisol, androgen and others are proteins that exist either exclusively in the cell nucleus or are partitioned between the cytoplasm and nucleus. Typically, the steroid receptor contain DNA binding domain at its 5' end and the ligand binding domain at its 3' end. The ligand is either the steroid hormone or steroid vitamin.

These nuclear proteins receptors specifically bind physiologically important molecules, namely their corresponding steroid hormones and vitamins.

Steroid hormones, which include 1,25-dihydroxyvitamin $D_3$, generate biological responses primarily by stimulating the synthesis of mRNA at the level of the initiation of gene transcription.

The binding of ligands to nuclear receptors leads to conformational changes in the receptor (*J. Biol. Chem.*, 270: 10551 (1995)), that promote formation of heterodimers with the retinoid X receptor (*Mol. Endocrinol.*, 10: 1617 (1995) and enhance binding to DNA coactivators (*Mol. Endocrinol.*, 5: 1815 (1991), and transcriptional activation (*Genes and Development*, 12: 1787 (1998).

As described above, binding of the cognate ligands to the nuclear receptors leads to conformational changes in the receptor that promote formation of heterodimers with the retinoid X receptor (RXR), and thereby enhance binding to DNA coactivators, which result in effective transcriptional activation, that is to a stimulation of gene transcription with the appearance of new messenger RNAs coding for proteins related to the ultimate biological response.

The three-dimensional x-ray structure for six nuclear receptors has been previously determined. These include the thyroid hormone receptor (TR), retinoic acid receptor (RAR), the estrogen receptor (ER), the progesterone receptor (PR) and the ligand binding and co-activator assembly of the peroxisome proliferator-activated receptor (PPAR). These structures have all been determined with their respective bound ligands. For the ER LBD, an x-ray structure is also known with the bound ligand raloxifene, a tissue-specific antagonist of the transcriptional activation function of the ligand-receptor complex. The x-ray structure is known for the LBD of the unoccupied 9-cis retinoic acid receptor.

While the structural aspects of all six protein LBDs were found to be remarkably similar with respect to their basic secondary and tertiary structural elements, details of the interior surface of the LBD which directly interacts with the appropriate cognate ligand are different for all receptors.

Nuclear receptor ligands and ligand binding domains, particularly that of thyroid receptor are disclosed in the PCT application PCT/US/96/20778, filed on Dec. 13, 1996, incorporated by reference. Selective thyroid hormone analogs are disclosed in U.S. Pat. No. 5,883,294, incorporated by reference. In vitro method of evaluating the antagonistic and agonistic effect of receptor-binding ligands is disclosed in the U.S. Pat. No. 5,578,445, incorporated by reference.

Vitamin $D_3$ analogs and their therapeutic utility is disclosed in the copending application Ser. No. 09/074,565, filed on May 6, 1998 and Ser. No. 09/073,723, filed on May 6, 1998, both incorporated by reference.

Vitamin $D_3$ (1α,25 dihydroxyvitamin $D_3$) belongs to the family of steroid receptors. However, its three-dimensional x-ray structure has not been previously determined.

It is, therefore, a primary objective of this invention to describe a three-dimensional x-ray structure model for ligand binding domain of the human nuclear receptor and its optimal orientation permitting identification and generation of pharmacologically active vitamin $D_3$ ligands.

All cited patents, patent applications and publication are hereby incorporated by reference.

SUMMARY

One aspect of the current invention is a three-dimensional model for residues 142–427 of the ligand binding domain of the human nuclear receptor for 1α,25-dihydroxyvitamin $D_3$.

Another aspect of the current invention is a method for selection of suitable vitamin $D_3$ analogs and ligands binding to the 1α,25-dihydroxyvitamin $D_3$ receptors.

Still another aspect of the current invention is a three dimensional x-ray structure model of the nuclear receptor for 1α,25-dihydroxyvitamin $D_3$.

Definitions

As defined herein:

"1α,25(OH)$_2$D$_3$" or "vitamin $D_3$" means 1α,25-dihydroxyvitamin $D_3$.

"VDR LBD" means ligand binding domain of the vitamin $D_3$ receptor.

"LBD" means ligand binding domain.

"VDR" means vitamin $D_3$ receptor.

"ER" means estrogen receptor.

"TR" means thyroid receptor.

"RAR" means retinoic acid receptor.

BRIEF DESCRIPTION OF DRAWINGS

FIGS. 1A and B illustrates a simplified version of the vitamin D endocrine system including the categories of target organs where biological responses are generated through vitamin $D_3$ ligands. Specifically listed are tissues which possess the nuclear receptor for 1α,25(OH)$_2$ vitamin $D_3$.

FIG. 2 illustrates the conformational flexibility of vitamin $D_3$ molecules using 1α,25(OH)$_2$D$_3$ as an example. Side chain (FIG. 2A), rotation around the 6, 7 carbon bond (FIG. 2B), and A-ring chain (FIG. 2C) conformations.

FIG. 3 also illustrates mediation of the slow nuclear and rapid biological responses by $1\alpha,25(OH)_2D_3$ and its conformationally flexible and conformationally restricted analogs in correlation to potential target cells and therapeutical treatment modalities.

FIG. 5 is alignment of a portion of the vitamin D receptor ligand binding domain (VDR LBD) with thyroid receptor ligand binding domain.

FIG. 7 illustrates the conformational flexibility of vitamin D molecules represented by $1\alpha,25(OH)_2D_3$.

DETAILED DESCRIPTION OF THE INVENTION

Figure 3:
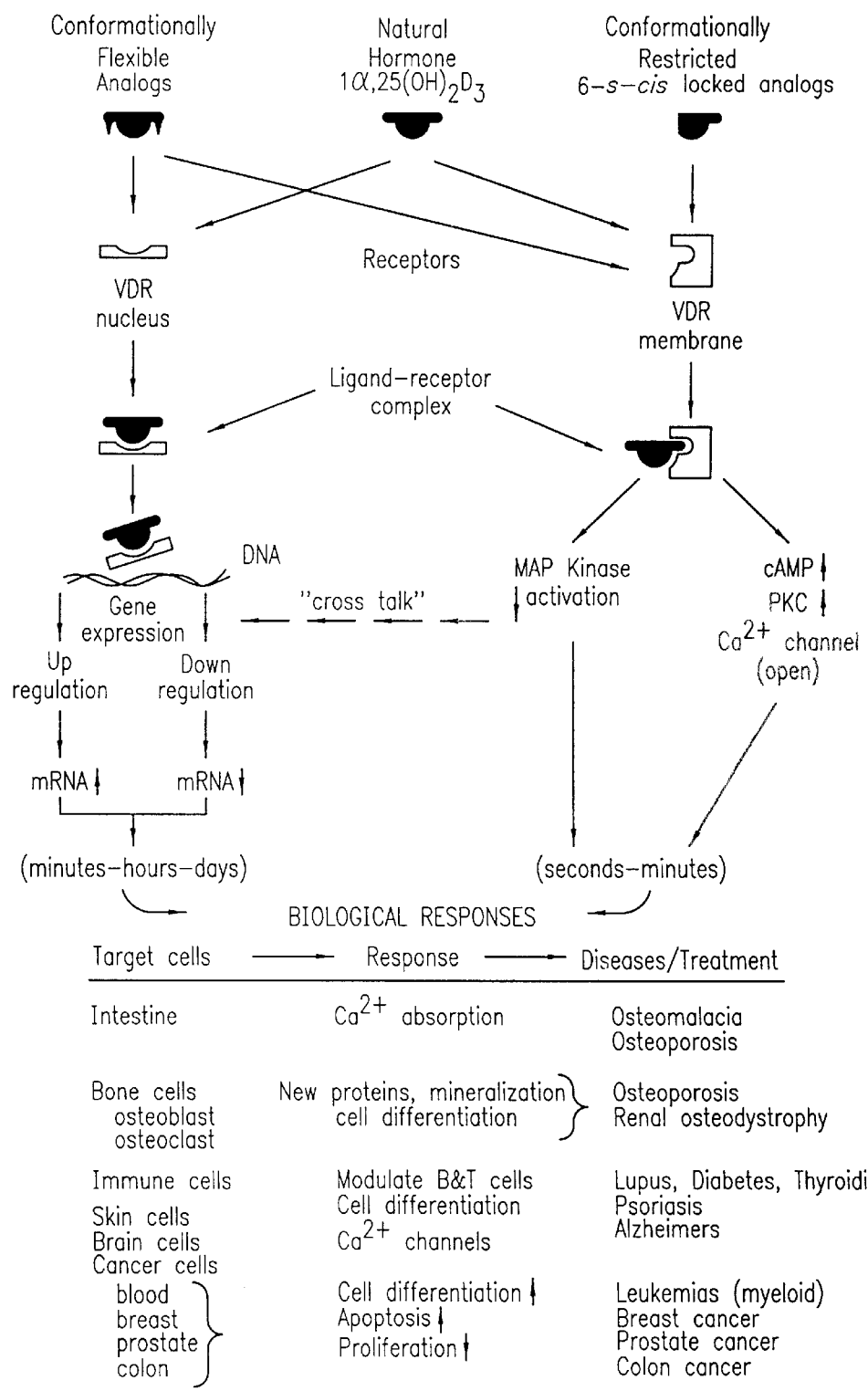
FIG. 3 illustrates both the central role of the nuclear and membrane receptors for $1\alpha,25(OH)_2D_3$ in mediating selective biological responses and the sites of action of both conformationally flexible and conformationally restricted analogs.

The current invention concerns the nuclear receptor for the $1\alpha,25$,dihydroxyvitamin $D_3$, its ligand binding domain, three dimensional model of the vitamin $D_3$ nuclear receptor, and the modeling of the biological actions of the vitamin D receptor (VDR).

The model is useful in a method for designing, selection and generation of suitable vitamin $D_3$ analogs and ligands binding to vitamin $D_3$ receptor and asserting specific pharmacological actions.

The biological action of the VDR is dependent upon its interaction with the functionally active ligand $1\alpha,25$-dihydroxyvitamin $D_3$ or its analog.

I. Biological Importance of Vitamin D and its Metabolites

Vitamin D is one of the most important biological regulators of calcium metabolism and is, therefore, essential for life in higher animals. Along with the two peptide hormones, parathyroid hormone and calcitonin, vitamin D is responsible for the minute-by-minute, as well as the day-to-day, maintenance of calcium/mineral homeostasis. These important biological effects are achieved as a consequence of metabolism of vitamin D metabolism into a family of biologically active metabolites.

A. $1\alpha,25$-Dihydroxyvitamin $D_3$ and Analogs

One of the vitamin D metabolites, namely $1\alpha,25$ dihydroxyvitamin $D_3$ ($1\alpha,25(OH)_2D_3$) is considered to be a steroid hormone. Therefore, the number of the biological responses attributable to the parent vitamin D occur in a steroid hormone-like fashion.

$1\alpha,25(OH)_2D_3$, which is primarily involved in mineral homeostasis, additionally acts on tissues not primarily related to mineral metabolism, such as, for example, on cell differentiation and proliferation including interaction with cancer cells detectable in leukemia, breast, prostate, colon tumor growth, the immune system, skin, selected brain cells, and also participates in the process of peptide hormone secretion exemplarized by parathyroid hormone or insulin.

The scope of the biological responses related to vitamin D is best understood through the schematic illustration of the vitamin D endocrine system as seen in FIG. 1. Vitamin $D_3$ itself is, in reality, only a prohormone and is not known to have any intrinsic biological activity. It is only after vitamin $D_3$ is metabolized first into $25(OH)D_3$ in the liver and then converted into its metabolites $1\alpha,25(OH)_2D_3$ and $24R,25(OH)_2D_3$ by the kidney, that biologically active molecules are produced.

The core elements of the vitamin D endocrine system include the skin, liver, kidney, blood circulation and the target organs. Photoconversion of vitamin D (7-dehydrocholesterol) to vitamin $D_3$, which is activated 7-dehydrocholesterol, is dependent on sunlight and occurs in the skin. Alternatively, vitamin $D_3$ can be supplied by the dietary intake. Vitamin $D_3$ is then metabolized by the liver to $25(OH)D_3$, the major form of vitamin D circulating in the blood. The kidney, functioning as an endocrine gland, converts $25(OH)D_3$ to the two principal dihydroxylated metabolites, namely $1\alpha,25(OH)_2D_3$ and $24R,25(OH)_2D_3$.

The hydrophobic vitamin D and its metabolites, particularly $1\alpha,25(OH)_2D_3$, are bound to the vitamin D binding protein (DBP) present in the plasma and systemically transported to distal target organs, as seen in the lower part of FIG. 1. $1\alpha,25(OH)_2D_3$ then binds to the target organs cell receptors and such binding is followed by the generation of appropriate biological responses through a variety of signal transduction pathways.

$1\alpha,25(OH)_2D_3$ and its functionally active analogs generate biological responses that can be utilized in the treatment of specified disease states. FIG. 1 identifies cells containing the nuclear receptor [$VDR_{nuc}$] for $1\alpha,25(OH)_2D_3$ generating genomic responses as well as the tissue location of the membrane receptor [$VDR_{mem}$] where rapid responses are initiated. The target sites for action of $1\alpha,25(OH)_2D_3$ agonist and antagonist analogs are also shown.

Certain types of biological actions of $1\alpha,25$-dihydroxyvitamin $D_3$ ligand or its analogs are achieved through the ligand binding with nuclear receptor ligand binding domain. Identification of the $1\alpha,25$-dihydroxyvitamin $D_3$ analogs binding to the vitamin D receptor binding domain is possible only if the receptor ligand binding domain is identified.

This invention, therefore, concerns a three dimensional model of the vitamin $D_3$ nuclear receptor and identification of ligand binding domain useful for selection of biologically active analogs of $1\alpha,25(OH)_2D_3$.

C. Conformational Flexibility of $1\alpha,25$-Dihydroxyvitamin D Analogs

Vitamin D is a seco steroid. Its 9,10 carbon-carbon bond is broken thus generating light carbon side chain. Because of the presence of the eight carbon side chain, both the parent vitamin D and all its metabolites and analogs are unusually conformationally flexible. Such conformational flexibility is seen in FIG. 2.

In biological systems, many shapes of $1\alpha,25(OH)_2D_3$ are available to interact with receptors to generate biological responses. Different shapes of $1\alpha,25(OH)_2D_3$ are recognized via different ligand binding domains present on the $VDR_{nuc}$, $VDR_{mem}$, and DBP.

FIG. 2 illustrates a general model of the conformational flexibility of $1\alpha,25(OH)_2D_3$. The specific model of vitamin $D_3$ nuclear receptor for determination of biologically active analogs binding to the ligand binding domain of vitamin $D_3$ nuclear receptor according to the invention is seen in FIG. 7.

FIG. 2A shows the dynamic single bond rotation of the cholesterol-like side chain of $1\alpha,25(OH)_2D_3$, that has 360° rotations about five single carbon bonds and the oxygen as indicated by the curved arrows. The dots in FIG. 2A indicate the position in three-dimensional space of the 25-hydroxyl group for some 394 readily identifiable side chain conformations which have been determined from energy minimization calculations. Two orientations of the C/D side chain are seen in FIG. 2A-1, a top view in FIG. 2A-2, and in plane view in FIG. 2A-3.

FIG. 2B shows the rapid (thousands of times per second) chair-chair interconversion of the A-ring of the secosteroid which effectively equilibrates the $1\alpha$,-hydroxyl between the axial (FIG. 1B-1) and equatorial (2B-2) orientations.

FIG. 2C shows the 360° rotational freedom about the 6,7 carbon-carbon bond of the seco B-ring which generates conformations ranging from the more steroid-like (6-s-cis) conformation, to the open and extended (6-s-trans) conformation of $1\alpha,25(OH)_2D_3$.

Conformationally flexible analogs of $1\alpha,25(OH)_2D_3$, as seen in FIG. 2, can interact with both the $VDR_{nuc}$ and the $VDR_{mem}$ while 6-s-cis locked conformationally restricted analogs interact only with the $VDR_{mem}$. Conformationally flexible analogs which bind to the vitamin $D_3$ nuclear receptor are typically agonists and typically, but not always, generate genomic responses.

A tabulation of the analogs of the invention, their conformational flexibility and general biological properties are presented in Table 1. As seen in Table 1, 6-s-cis locked conformationally restricted analogs JM, JN, JO and JP do not generate genomic responses and would not bind to the vitamin $D_3$ nuclear receptor.

TABLE 1

Properties of Analogs of $1\alpha,25(OH)_2D_3$

| Code | Analog Name | Conformation | Genomic Response | Rapid Response | Antagonist |
|---|---|---|---|---|---|
| C | $1\alpha,25(OH)_2D_3$ | Flexible | Yes | Yes | No |
| DE | 22-(m-hydroxyphenyl) $1\alpha,25(OH)_2D_3$ | Flexible | Yes | Yes | No |
| DF | 22-(p-hydroxyphenyl) $1\alpha,25(OH)_2D_3$ | Flexible | Yes | Yes | No |
| EV | 22-(m-dimethylhydroxymethyl)phenyl-23,24,25,26,27-pentanor-$1\alpha(OH)D_3$ | Flexible | Yes | Yes | No |
| GE | 14-epi-$1\alpha,25(OH)_2D_3$ | Flexible | Yes | Yes | No |
| GF | 14-epi-$1\alpha,25(OH)_2$-pre-$D_3$ | Flexible | Yes | Yes | No |
| HH | $1\beta,25(OH)_2$-epi-$D_3$ | Flexible | No | No | Yes |
| HJ | $1\alpha,25(OH)_2$-epi-$D_3$ | Flexible | Yes | Yes | No |
| HL | $1\beta,25(OH)_2D_3$ | Flexible | No | No | Yes |
| HQ | (22S)-$1\alpha,25(OH)_2$-22,23-diene-$D_3$ | Flexible | Yes | Yes | No |
| HR | (22R)-$1\alpha,25(OH)_2$-22,23-diene-$D_3$ | Flexible | Yes | Yes | No |
| HS | $1\alpha,18,25(OH)_2D_3$ | Flexible | Yes | Yes | No |
| IB | 23-(m-dimethylhydroxymethyl)phenyl-22-yne-24,25,26,27-tetranor-$1\alpha OH)D_3$ | Flexible | Yes | Yes | No |
| JM | $1\alpha,25(OH)_2$-7-dehydrocholesterol | 6-s-cis locked | No | Yes | No |
| JN | $1\alpha,25(OH)_2$-7-lumisterol | 6-s-cis locked | No | Yes | No |
| JO | $1\alpha,25(OH)_2$-pyrocalciferol | 6-s-cis locked | No | Yes | No |
| JP | $1\alpha,25(OH)_2$-isopyrocalciferol | 6-s-cis locked | No | Yes | No |
| JR | $1\alpha,25(OH)_2$-7,8-cis-$D_3$ | Flexible | Yes | Yes | No |
| JS | $1\alpha,25(OH)_2$-5,6-trans-7,8-cis-$D_3$ | Flexible | Yes | Yes | No |
| JV | (1S, 3R, 6S)-7,19-retro-$1\alpha,25(OH)_2D_3$ | Flexible | Yes | Yes | No |
| JW | (1S, 3R, 6R)-7,19-retro-$1\alpha,25(OH)_2D_3$ | Flexible | Yes | Yes | No |
| JX | 22-(p-hydroxyphenyl)-,23,24,25,26,27-pentanor-$D_3$ | Flexible | Yes | Yes | No |
| JY | 22-(m-hydroxyphenyl)-,23,24,25,26,27-pentanor-$D_3$ | Flexible | Yes | Yes | No |
| LO | $14\alpha, 15\alpha$-methano-$1\alpha,25(OH)_2D_3$ | Flexible | Yes | Yes | No |

C. Vitamin $D_3$ Receptors

The spectrum of biological responses mediated by the hormone $1\alpha,25(OH)_2D_3$ occurs as a consequence of the interaction of $1\alpha,25(OH)_2D_3$ with two classes of specific receptors. These receptors are identified as the nuclear receptor ($VDR_{nuc}$), and the cellular membrane receptor, ($VDR_{mem}$).

The $1\alpha,25(OH)_2D_3$ nuclear receptor ($VDR_{nuc}$) from several species has been characterized both biochemically and biologically. The $VDR_{nuc}$ protein was determined to have a molecular weight of about 50 kDa. Through cloning, the $VDR_{nuc}$ was shown to belong to the super family of proteins that includes receptors for all of the classical steroid hormones, such as estradiol, progesterone, testosterone, glucocorticoids, mineralocorticoids, thyroxine and retinoids. The $VDR_{nuc}$ protein contains a ligand binding domain able to bind with high affinity and with great specificity $1\alpha,25(OH)_2D_3$ and its closely related conformationally flexible analogs.

Different shapes of the conformationally flexible $1\alpha,25(OH)_2D_3$ or its analogs bind to the $VDR_{nuc}$ and $VDR_{mem}$ and initiate biological responses via activation of signal transduction mechanisms which are coupled to either the $VDR_{nuc}$ or the $VDR_{mem}$. Thus the totality of biological responses mediated by $1\alpha,25(OH)_2D_3$ or its analogs represents an integration of both nuclear receptor and membrane receptor initiated events. However, this invention is directed solely to the nuclear receptor $VDR_{nuc}$.

In terms of analogs of $1\alpha,25(OH)_2D_3$ which act as $VDR_{nuc}$ ligands, there are two general classes of such analogs. Agonist analogs generate responses similar to $1\alpha,25(OH)_2D_3$ Antagonist analogs block or minimize the responses initiated by $1\alpha,25(OH)_2D_3$ or agonist analogs. Further, agonist or antagonist molecules can either be fully conformationally flexible, like the natural hormone $1\alpha,25(OH)_2 D_3$, or exceptionally be conformationally restricted. Conformationally flexible agonists or antagonists bind to the vitamin $D_3$ nuclear receptor while most of the conformationally restricted agonists or antagonist do not.

A detailed list of the conformationally flexible agonist and antagonist analogs is presented in Tables 2 and 3. Some conformationally flexible analogs can interact with both $VDR_{nuc}$ and $VDR_{mem}$.

FIG. 3 illustrates the mechanisms of action by which $1\alpha,25(OH)_2D_3$ generates biological responses in target cells. As indicated at the top of FIG. 3, the conformationally flexible natural hormone, $1\alpha,25(OH)_2D_3$, and its conformationally flexible analogs interact with both the $VDR_{nuc}$ and $VDR_{mem}$. However, 6-s-cis locked, that is, conformationally restricted analogs can interact only with the $VDR_{mem}$. After occupancy of the receptors by their ligand, appropriate signal transduction systems are initiated which ultimately lead to the generation of biological responses. The bottom panel of the FIG. 3 lists certain target cells for $1\alpha,25(OH)_2D_3$ and identifies typical responses of these cells to administration of $1\alpha,25(OH)_2D_3$ or the analog which occur there. Disease states responding to treatment with analogs of $1\alpha,25(OH)_2D_3$ are also listed in FIG. 3, bottom.

The binding of the analog or $1\alpha,25(OH)_2D_3$ to $VDR_{nuc}$ receptor leads to modulation of gene transcription, that is, to gene expression up-regulation or down-regulation as seen on the left side of FIG. 3.

D. Therapeutically Active Analogs of $1\alpha,25(OH)_2D_3$

Therapeutically active analogs of $1\alpha,25(OH)_2D_3$ are either agonists or antagonists.

1. Agonists (a) Conformationally Flexible Genomic Agonist Analogs

Conformationally flexible genomic agonist analogs are the analogs which interact with the nuclear receptor for $1\alpha,25(OH)_2D_3$ $VDR_{nuc}$ and are, therefore, involved in the slow genomic responses. Exemplary analogs in this group are analogs listed in Table 2. A two-letter code name for analog chemical identification is designated followed by the chemical name.

TABLE 2

| | |
|---|---|
| DE | 22-(m-hydroxyphenyl)-23,24,25,26,27-pentanor-1α(OH)D$_3$ |
| DF | 22-(p-hydroxyphenyl)-23,24,25,26,27-pentanor-1α(OH)D$_3$ |
| EV | 22-(m-dimethylhydroxymethyl)phenyl)-23,24,25,26,27-pentanor-1α(OH)D$_3$ |
| GE | 14-epi-1α,25(OH)$_2$D$_3$ |
| GF | 14-epi-1α,25(OH)2-pre-D$_3$ |
| HJ | 1α,25(OH)$_2$-3-epi-D$_3$ |
| HQ | (22S)-1α,25(OH)$_2$-22,23-diene-D$_3$ |

TABLE 2-continued

| | |
|---|---|
| HR | (22R)-1α,25(OH)$_2$-22,23-diene-D$_3$ |
| HS | 1α,18,25(OH)$_3$D$_3$ |
| IB | 23-(m-(Dimethylhydroxymethyl)phenyl)-22-yne-24,25,26,27-tetranor-1α(OH)D$_3$ |
| JR | 1α,25(OH)$_2$-7,8-cis-D$_3$ |
| JS | 1α,25(OH)$_2$-5,6-trans-7,8-cis-D$_3$ |
| JV | (1S,3R,6S)-7,19-retro-1α,25(OH)$_2$D$_3$ |
| JW | (1S,3R,6R)-7,19-retro-1α,25(OH)$_2$D$_3$ |
| JX | 22-(p-hydroxyphenyl)-22,23,24,25,26,27-pentanor-D$_3$ |
| JY | 22-(m-hydroxyphenyl)-23,24,25,26,27-pentanor-D$_3$ |
| LO | 14α,15α-methano-1α,25(OH)$_2$D$_3$ |

(b) Conformationally Restricted Genomic Agonist Analogs

In addition to the conformationally flexible agonists, there exists also a group of conformationally restricted genomic agonists. Conformationally restricted genomic agonist analogs are the analogs which bind with a high specificity to the vitamin D nuclear receptor $VDR_{nuc}$ and are therefore also involved in genomic responses.

(c) Conformationally Flexible Nongenomic Agonist Analogs Generating Rapid Response Conformationally flexible agonist analogs of $1\alpha,25(OH)_2D_3$ which stimulate genomic as well as rapid nongenomic responses via interaction with the vitamin D nuclear membrane receptor are listed in Table 3.

TABLE 3

| | |
|---|---|
| DE | 22-(m-hydroxyphenyl)-23,24,25,26,27-pentanor-1α(OH)D$_3$ |
| DF | 22-(p-hydroxyphenyl)-23,24,25,26,27-pentanor-1α(OH)D$_3$ |
| EV | 22-(m-(dimethylhydroxymethyl)phenyl)-23,24,25,26,27-pentanor-1α(OH)D$_3$ |
| GE | 14-epi-1α,25(OH)$_2$D$_3$ |
| GF | 14-epi-1α,25(OH)$_2$-pre-D$_3$ |
| HJ | 1α,25(OH)$_2$-3-epi-D$_3$ |
| HQ | (22S)-1α,25(OH)$_2$-22,23-diene-D$_3$ |
| HR | (22R)-1α,25(OH)$_2$-22,23-diene-D$_3$ |
| HS | 1α,18,25(OH)$_3$D$_3$ |
| IB | 23-(m-(dimethylhydroxymethyl)phenyl)-22-yne-24,25,26,27-tetranor-1α(OH)D$_3$ |
| JR | 1α,25(OH)$_2$-7,8-cis-D$_3$ |
| JS | 1α,25(OH)$_2$-5,6-trans-7,8-cis-D$_3$ |
| JV | (1S,3R,6S)-7,19-retro-1α,25(OH)$_2$D$_3$ |
| JW | (1S,3R,6R)-7,19-retro-1α,25(OH)$_2$D$_3$ |
| JX | 22-(p-hydroxyphenyl)-22,23,24,25,26,27-pentanor-D$_3$ |
| JY | 22-(m-hydroxyphenyl)-23,24,25,26,27-pentanor-D$_3$ |
| LO | 14α,15α-methano-1α,25(OH)$_2$D$_3$ |

2. Antagonists (a) Conformationally Flexible Antagonists of Genomic Responses

Conformationally flexible antagonist of genomic responses function as antagonists of the vitamin D nuclear receptor. Exemplary of the conformationally flexible antagonist is the analog HH (see Table 1).

The biological actions of the $1\alpha,25(OH)_2D_3$ are generated principally as a consequence of its interaction with the nuclear vitamin D receptor ($VDR_{nuc}$) which is known to involve regulation of transcription of genes associated with the generation of biological responses.

This invention describes the generation of a three dimensional model for the VDR LBD based on the x-ray crystallographic structure of the TR LBD. This VDR model is evaluated with respect to a number of ligand-receptor structure function topics.

II. Vitamin D Nuclear Receptor

As described above, vitamin $D_3$ ($1\alpha,25(OH)_2D_3$) nuclear receptor belongs to the family of steroid receptors. These receptors are considered to be transcription factors which, in response to their activation resulting from hormone or vitamin binding, initiate gene transcription and stimulate the synthesis of mRNA.

Vitamin $D_3$ nuclear receptor is a protein of approximately 50 kD which is comprised of a known primary amino acid sequence of 427 amino acids. The mode of action of vitamin D nuclear receptor is illustrated in FIG. 4.

Figure 4:
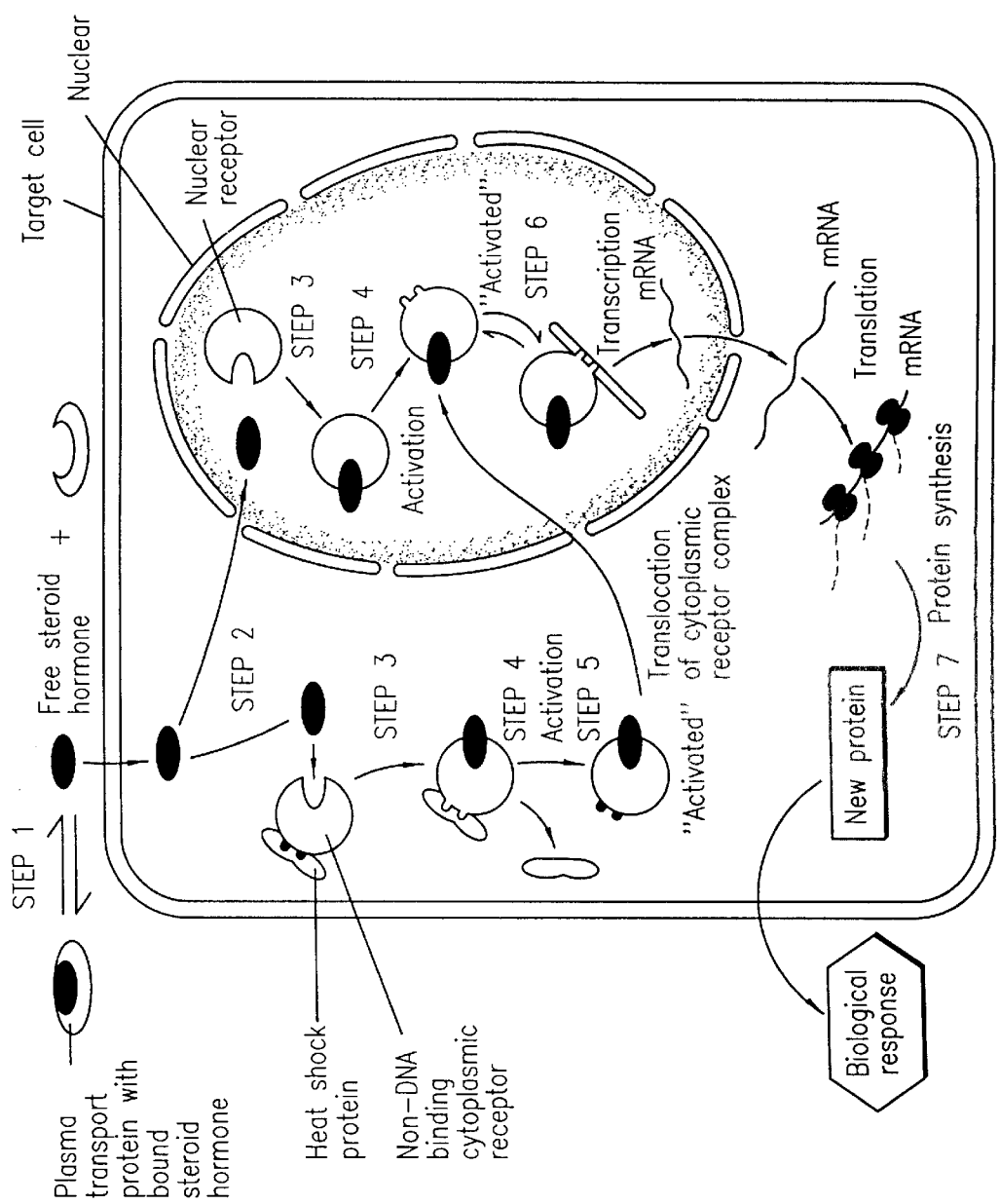
FIG. 4 is a schematic model of mode of action of $1\alpha,25$-dihydroxyvitamin $D_3$ on a nuclear receptor.

FIG. 4 summarizes, in a generic fashion, the sequence of events, herein called steps, that occur after the arrival of the $1\alpha,25$-dihydroxy vitamin $D_3$ at its target cell. Involvement of the receptor is clearly shown.

In step 1, $1\alpha,25(OH)_2D_3$ dissociates from the vitamin D binding protein (DBP) present in plasma. In step 2, the $1\alpha,25(OH)_2D_3$ enters the target cell by diffusing through the outer cell membrane. Then, depending upon the subcellular localization of the unoccupied receptor, $1\alpha,25(OH)_2D_3$ either interacts with the receptor in the cytoplasmic compartment or crosses through the cytoplasm and the perinuclear membrane to interact with a nuclear receptor in the nucleus. Subcellular localization of $1,25(OH_2)D_3$ has been found to be 75% in the nucleus and 25% in the cytoplasm.

The unoccupied form of the vitamin $D_3$ receptor is believed to exist in the cell as a conjugate with a dimer of the 90-kDa heat shock protein (HSP). In FIG. 4 the HSP dimer is indicated by a pair of ovals.

In steps 3 and 4, the receptor becomes transformed or activated as a consequence of release of the 90-kDa HSP and binding of its cognate ligand, so that the DNA-binding domain is now exposed (activated). In step 5, the cytoplasmic activated receptor translocates to the nucleus, probably through a nucleopore. Then in step 6, the activated nuclear receptor, or more likely a heterodimer of the receptor, seeks out the correct sequence of DNA that will allow it to form a high-affinity complex between the receptor and the $1\alpha,25(OH)_2D_3$ response elements (VRE) of the promoters of a selected set of genes and also any required transcription factors.

As a consequence of the activated receptor binding to the promoters, either induction or repression of the $1\alpha,25(OH)_2D_3$ gene will occur, leading to more or less of the mRNA coded for the $1\alpha,25(OH)_2D_3$ gene. The newly transcribed mRNAs are translocated to the cytoplasm where they become incorporated into polysomes and undergo translation (step 7) resulting in protein synthesis. In the final step 8, the increased or decreased amount of new synthesized proteins generates the greater or lesser biological response (s) dictated by $1\alpha,25(OH)_2D_3$ in specific target cells. As seen in FIG. 1, large array of biological responses can be modulated depending upon the phenotype of the target cell that possesses the $1\alpha,25(OH)_2D_3$ receptor.

III. Three-Dimension Model of Vitamin $D_3$ Nuclear Receptor

In order to provide a useful tool for selection, designing and predicting a biological action of $1\alpha,25$-dihydroxy vitamin $D_3$ analogs, a three dimensional model of the $1\alpha,25$-dihydroxy vitamin $D_3$ nuclear receptor ligand binding domain was generated.

Although three-dimensional models for several other steroid hormones were previously described, as referenced above, until this invention, an x-ray structure model for $1\alpha,25$-dihydroxyvitamin $D_3$ nuclear receptor was not available to describe the three-dimensional structure of ligand binding domain (LBD) of the VDR.

This invention, therefore, in one aspect concerns a generation of the three-dimensional model for the LBD of the VDR.

A. The Three Dimensional Model

A three-dimensional model for residues 142–427 of the ligand binding domain (LBD) of the human nuclear receptor for $1\alpha,25$-dihydroxyvitamin $D_3$ (VDR) has been generated based on the x-ray crystallographic atomic coordinates of the LBD of the rat $\alpha 1$ thyroid receptor (TR).

The VDR LBD model has an elongated globular shape comprised of an antiparallel $\alpha$-helical triple sandwich topology, made up of 12 $\alpha$-helical elements linked by short loop structures. Collectively, these structural features were found to be similar to the characteristic secondary and tertiary structures for six nuclear receptors with known x-ray structures.

The detailed method used for generation of the LBD of the nuclear receptor for $1\alpha,25(OH)_2D_3$ is described in Example 1. The iterative approach for defining alignment(s) of the VDR LBD with the TR LBD was based on both the suggestion of a canonical structure for the LBD of nuclear receptors, described in *Nature Struct. Biol.*, 3: 87 (1996) (1995), and RAR x-ray structures which have a highly similar common fold, described in *Nature*, 378: 681 (1995).

B. VDR/TR Alignments

Three different VDR/TR alignments (A, B and C) were originally generated and compared using the Insight Homology program.

Although alignment A (not shown), achieved an exact alignment of 90 identical residues between the VDR and TR, it resulted in the arbitrary presence of 25 breaks in the VDR sequence. Accordingly, alignment A was rejected. Alignment B, which is seen in FIG. 5, was chosen over alignment C based on a greater number of identical (58 vs. 54) and conserved (75 vs. 70) residues between the VDR and TR, a smaller number of unassigned TR residue coordinates (10 vs. 12) and a smaller number of VDR residues without assigned coordinates (42 vs. 54).

FIG. 5 shows the appropriate alignments from VDR residue L224 (SEQ ID NO:1) and TR residue L212 (SEQ ID NO:2) to their respective carboxy terminus. These alignments differed in the size of a VDR loop (either 25 or 42 amino acids) which is positioned between helices 2 and 3.

Figure 6A:
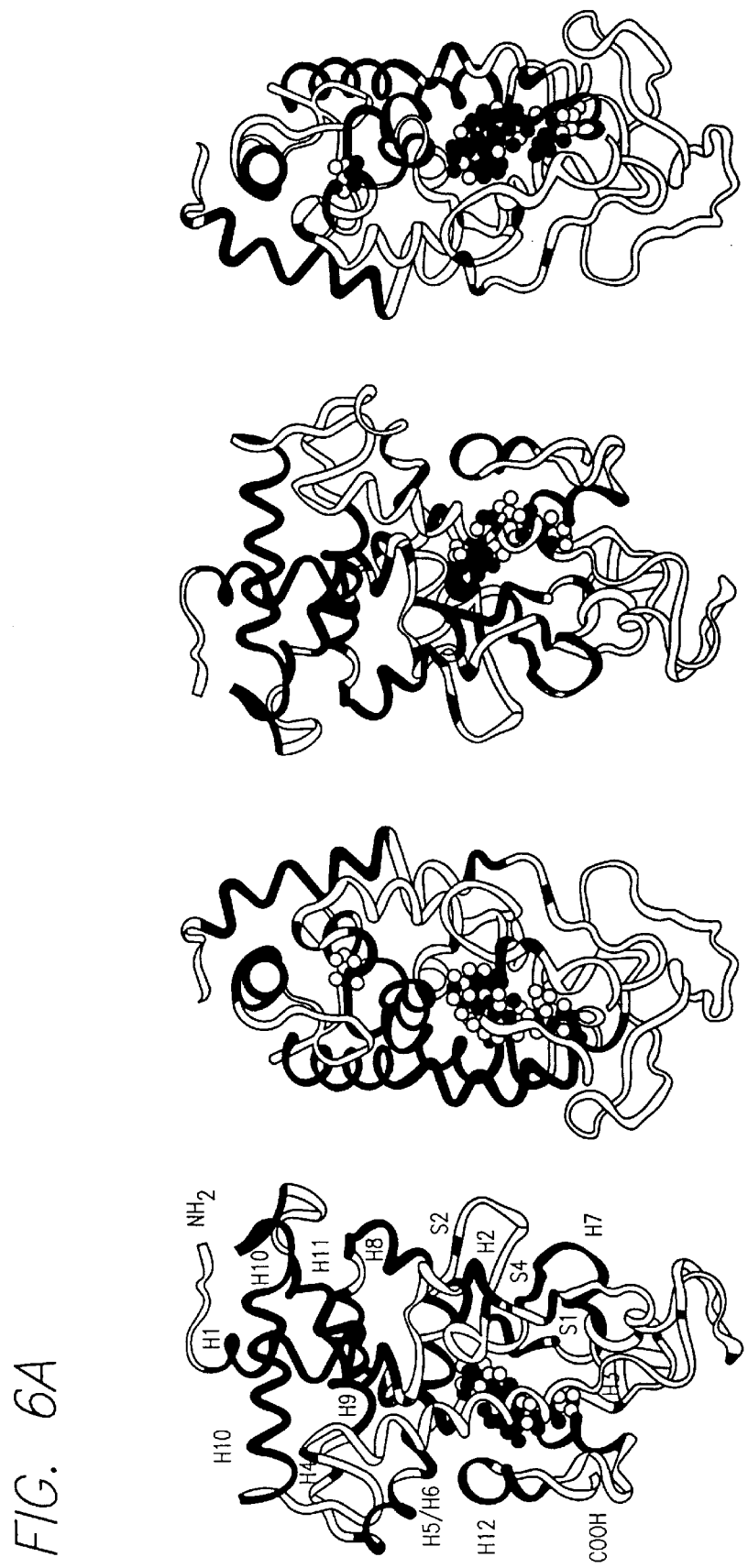
FIG. 6 is a three dimensional model of the VDR LBD. The four panels in FIG. 6A illustrate different representations of the same three-dimensional model of the VDR LBD and illustrate four successive 90° rotations around the vertical axis of the VDR model present on the left side.
FIG. 6B depicts $1\alpha,25(OH)_2D_3$ entering the VDR LBD.
FIG. 6C illustrates the positions of the six naturally occurring and five experimental mutations.
FIG. 6D shows a putative ligand-dependent GRIP1 coactivator binding site on the surface of the VDR.
FIGS. 6E, F, G and H present a comparison of the similarities and differences between four pairs of different configurations of the $1\alpha,25(OH)_2D_3$ molecules docked in the VDR LBD.
Figure 6H:
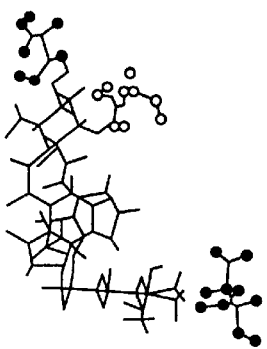

FIG. 5 presents the selected alignment B of the LBD of the VDR with the TR which was used to generate the three dimensional model of the VDR LBD. The amino acid sequence of the human VDR extends from residues 142 to 427. FIG. 5 describes only the ligand binding domain of the VDR from residues T142 to the carboxy terminal S427 and includes a loop of 25 residues from S199 to Q223 that could not be included in the alignment with the TR. The amino acid sequence of the rat $\alpha l$ TR structure that was used extends from residues 157 to 410 and describes only the TR LBD. The closed boxes indicate the position of the twelve $\alpha$-helices that are defined by the TR x-ray structure. The solid bars above the VDR sequence correspond to amino acid residues in the VDR which make close contact (3–4 A) with a portion of the docked ligand $1\alpha,25(OH)_2D_3$, as seen in FIG. 6A.

C. VDR Ligand Binding Domain

The VDR LBD model with $1\alpha,25(OH)_2D_3$ as the docked ligand is shown in FIG. 6, panels A and C. FIG. 6 is a three-dimensional model of the VDR LBD.

As seen in FIG. 6, the VDR protein model is an elongated globular shape comprised of an antiparallel helical triple sandwich topology, made up of 12 $\alpha$-helical elements linked by short loop structures. As pointed out above, these structural features are similar to the characteristic secondary and tertiary structures of the six nuclear receptors with the known x-ray crystal structures.

Since prolines are not normally found in α-helices, the presence of the P155, P156 proline doublet in the VDR suggests that helix 1 will be nonlinear. With respect to the VDR 'loop' region (S199-Q223), it was not possible to identify any secondary structure nor was there any sequence homology with domains seen on other proteins. The volume of the 1α,25(OH)$_2$D$_3$ ligand is 375 A$^3$ while that of the VDR LBD cavity available to the ligand is approximately 620 A$^3$.

FIG. 6 color photograph illustrates different representations of the same three-dimensional model of the VDR LBD. The ligand in each panel is 1α,25(OH)$_2$D$_3$. Its atoms are colored so that hydrogen is seen as grey, oxygen is seen as red and carbon is seen as green. The 1α,25(OH)$_2$D$_3$ is in a conformation close to the planar 6-s-cis shape of FIG. 7D. The A-ring is in the chair-conformer-A (FIG. 6B) where the 1α-OH is axial and the 3β-OH is equatorial. The side chain is oriented in its 'northeasterly' or 2 o'clock orientation as defined by its global minimum energy (see FIG. 6B 'dot map' with line tracing of the side chain).

FIG. 6A illustrates four successive 90° rotations around the vertical axis of the VDR model present on the left side. Each view illustrates a different perspective of the twelve helices (presented as ribbons) and four 13-strands that collectively define the LBD of the VDR.

The helices are numbered in the same order (H1–H12) as for the TR structure, seen in FIG. 5. Each helix has its own unique color that is retained in panels B and C.

The light white loop seen at the bottom of the VDR LBD model represents the 25 residues present between helices 2 and 3 termed 'VDR loop' in FIG. 5.

FIG. 6B depicts 1α,25(OH)$_2$D$_3$ (blue colored molecule) beginning to enter the VDR LBD. In this panel, the right side is an α-helix ribbon diagram and the left side is a CP space-filling representation.

The color coding of the 12 helices is the same as in FIG. 6A.

For both views of FIG. 6B, helix 12 (dark red) has been moved (compare with panel A) to duplicate its position in the RXRα structure which has an unoccupied LBD, as described in *Nature*, 375: 377 (1995). Thus the position of helix 12 reflects the 'open' portal property of an unoccupied receptor which contrasts with the 'closed' portal position of helix 12 in an occupied receptor seen in FIG. 6A. FIG. 6C illustrates one view (comparable to view of the left FIG. 6A) of the VDR LBD and illustrates the position of the six naturally occurring (colored blue) and five experimental (colored red) mutations. The amino acid residues are shown in a CP space-filling representation.

FIG. 6D illustrates a putative ligand-dependent GRIP1 coactivator binding site on the surface of the VDR. The two red residues are L417 and E420 (helix 12), the two green residues are 1260 and K264 (helix 5) and the two yellow residues are 1242 and K246 (helix 3). All residues but 1242 are conserved in the TR and several other nuclear receptors. The 1242 is a conservative substitution for a V230 in the TR. The formation of the GRIP1 coactivator binding site is achieved in the TR by the bringing together selected regions of helices 3, 5 and 12, which occurs after the receptor has bound an agonist ligand. This GRIP1 site is postulated to be stabilized via a salt bridge between residues K264 (helix 5) and E420 (helix 12).

FIGS. 6E, 6F, 6G and 6H compare the similarities and differences between four pairs of different configurations of the 1α,25(OH)$_2$D$_3$ molecules which are docked in the VDR LBD. Only three residues of the VDR LBD are illustrated. The two nominee hydrogen bond donors (yellow 5237 and blue 5275) for the 1α-OH and 3β-OH groups of the ligand, and T415 (dark red) as a hydrogen bond donor for the 25-OH group of 1α,25(OH)$_2$D$_3$.

In each of these four panels, the green ligand is 1α,25 (OH)$_2$-6s-cis-D$_3$ with the cyclohexane ring in the conformer A representation (designated A/cis). The cyclohexane ring of the green A-cis molecule is exactly superimposed with the A-ring chair conformer in each of the four different configurations of a magenta colored 1α,25(OH)$_2$D$_3$ molecule. The magenta ligand in FIGS. 6E, 6F, 6G and 6H is respectively 1α,25(OH)$_2$D$_3$ in an up-side-down B-cis (FIG. 6E), A-trans (FIG. 6F), up-side-down A-trans (FIG. 6G), and up-side-down B-trans (FIG. 6H) configuration.

D. Conformational Flexibility of 1α,25-dihydroxy Vitamin D$_3$ Molecules

The vitamin D$_3$ and all its metabolites, including the steroid hormone 1α,25(OH)$_2$D$_3$, are, in comparison to other steroid hormones, unusually conformationally flexible as illustrated in FIG. 7.

FIG. 7 illustrates conformational flexibility of vitamin D molecules using 1α,25(OH)$_2$D$_3$ as an example. FIG. 7A shows a structure of 1α,25(OH)$_2$D$_3$ indicating the three structural features of the molecule which confer (in relation to other steroids), unusual conformational flexibility upon the molecule. FIG. 7B shows the dynamic 360° side chain rotation about the five single carbon-carbon bonds, indicated by the curved arrows in FIG. 7A. The dots indicate the position in three-dimensional space of the 25-hydroxyl group for some 394 readily identifiable side chain conformations that have been determined from energy minimization calculations according to *J. Cell Biochem.*, 49: 10 (1992). The position of the side chain in its minimal energy state is indicated to be in the "northeast" (2 o'clock) orientation by the line tracing of the side chain.

Figure 7A:
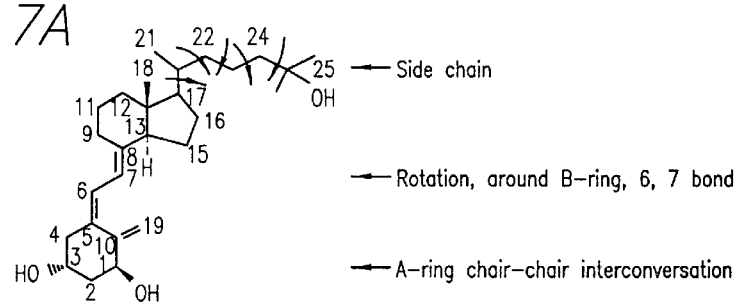
FIG. 7A shows three structural features of $1\alpha,25(OH)_2D_3$ which are responsible for unusual conformational flexibility of vitamin D molecules compared to other steroid hormones.
Figure 7B:
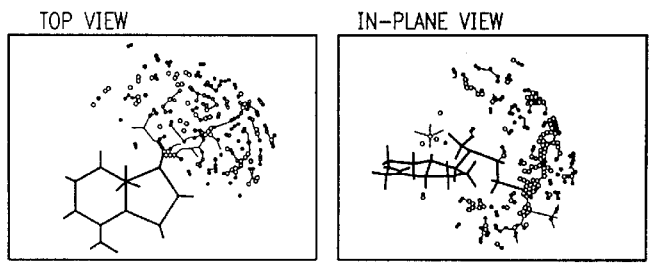
FIG. 7B shows side chain (left panel) and rotation around the 6, 7 carbon bond (right panel).
Figure 7C:
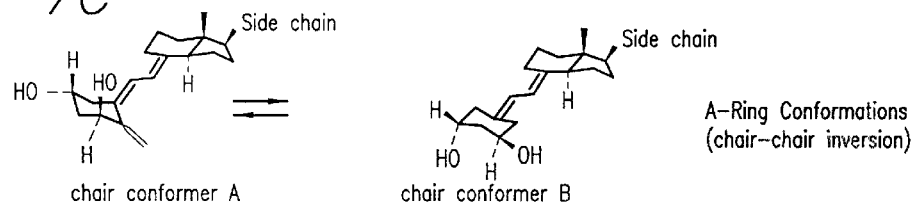
FIG. 7C shows the rapid chair-chair interconversion of the A-ring of the seco steroid.

FIG. 7C shows the rapid (thousands of times per second) chair-chair interconversion of the A-ring of the seco steroid which generates the distinct chair conformer A with the 19-methylene "down" [1α-OH axial, 3β-OH equatorial] and chair conformer B with the 19-methylene "up" (1α-OH equatorial, 3β-OH axial).

Figure 7D:
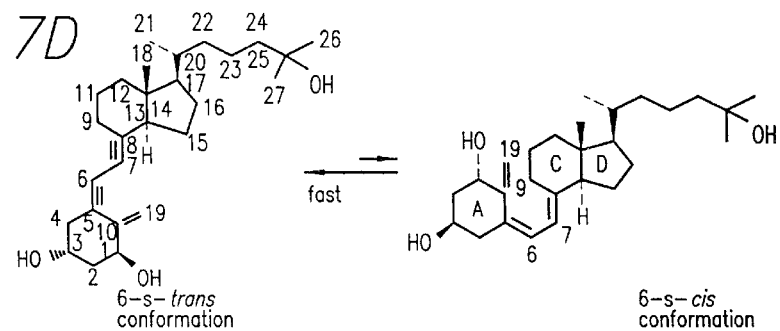
FIG. 7D illustrates the rapid 360° rotational freedom around the 6,7 single carbon bond of the seco B ring.

FIG. 7D shows the rapid 360° rotational freedom about the 6,7 single carbon-carbon bond of the seco B ring which generates conformations ranging from the more steroid-like (6-s-cis) conformation to the open and extended (6-s-trans) conformation of 1α,25(OH)$_2$D$_3$.

Figure 7E:
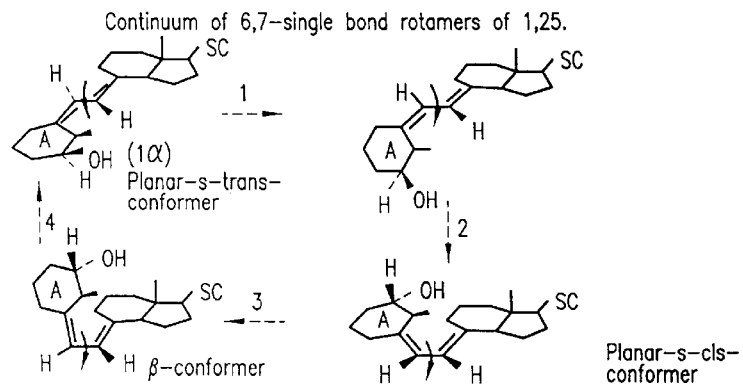
FIG. 7E shows four steps of successive 90° rotation around the 6,7 carbon-carbon bond.

FIG. 7E further illustrates the 360° rotation about the 6,7 carbon-carbon bond. Four steps of successive 90° rotations are shown. Each intermediate structure has a different shape, particularly with respect to the position of the critical 1α-hydroxyl and the plane of the A-ring in relation to the plane of the C/D-rings.

The issues regarding selection of the appropriate conformational shape of the 1α,25(OH)$_2$D$_3$ molecule to be docked into the LBD of the VDR are described in detail in the above FIG. 7. Direction of orientation of the ligand molecule in the VDR LBD (A-ring inward vs. side chain) was determined by reference to the orientation of ligands in the ER (*Nature* 389: 753, (1997)) and the PR (*PNAS* (USA), 95: 5998, (1998)). For both receptors, of which the ligands are classic steroids, the ligand A-rings were pointed toward the interior of the LBD cavity while the D rings were directed towards helix 12.

The interior surface of the VDR LBD, like the other nuclear steroid receptors, is comprised mostly of hydrophobic residues. The black bars shown in FIG. 5 along the VDR sequence identify sixteen, mostly hydrophobic, residues that are within 3–4 Å of the docked ligand.

E. Interior Surface of the VDR LBD

Evaluation of the interior surface of the LBD for potential hydrogen bond donors for interaction with the three hydroxyl groups of $1\alpha,25(OH)_2D_3$ indicated a bimodal distribution of hydrophilic residues at the end of the LBD. Thus nominee hydrogen bond donors for the A-ring $1\alpha$-OH and $3\beta$-OH groups include S235, S237 and S275, while residues H305, S306, Y401, S405, and T415 are obvious nominees for hydrogen bonding with the side chain 25-OH group.

The $1\alpha,25(OH)_2D_3$ ligand shown in FIG. 6 has its $1\alpha$-OH, $3\beta$-OH and 25-OH docked near S237, S275 and Y401 of the VDR LBD, respectively. This has the consequence of having the A-ring oriented 'in', that is towards the interior of the LBD and the side chain oriented 'out', that is towards helix 12, the site of the AF-2 domain.

When the four ribbon views of the VDR (FIG. 6A) were converted to CP space-filling views (data not shown), no hint of the ligand was apparent on the VDR surface, nor was there any obvious entrance portal discernable for the ligand.

The ligands of all the nuclear receptors are completely buried in the interior of their cognate receptors. The route by which the ligand gain access to the LBD cavity was investigated comparing the x-ray structure of the unoccupied RXR with the occupied RAR. The only significant difference found was in the different positions of helix 12. As a consequence, two conformational states for the apo and holo-LBDs of nuclear receptors were proposed.

In the unoccupied receptor, helix 12 is rotated out and down to create an open portal, while in the occupied receptor, helix 12 is rotated up to interact with helices 3 and 5. Such rotation has the consequence of closing the portal. FIG. 7B presents the open portal view of the VDR in both the ribbon and CP space-filling views. The contrasting closed portal views of the VDR are seen in FIG. 7D.

Table 4 summarizes 6 natural and 5 experimental mutations in the LBD of the VDR that have identified amino acids critical for normal LBD function.

TABLE 4

| Mutation | Consequences |
| --- | --- |
| C190W♦ | Familial VDDR-II syndrome |
| F244G | Impaired transactivation |
| L254G | Impaired transactivation; No RXR heterodimers |
| R274L♦ | Impaired ligand binding; |
| C288G | VDRR-II syndrome |
| Y295 stop♦ | Premature termination; no ligand binding |
| H305Q♦ | 80% decrease in ligand binding and decreased transactivation |
| I314S♦ | Impaired ligand retention, RXR dimerization and transactivation |
| R391C♦ | Impaired RXR dimerization and transactivation |
| L417A | Impaired transactivation by either mutation |
| E420A | |

The mutations in the LBD of the VDR are listed sequentially from the amino terminus to the carboxyl terminus of the VDR LBD.

♦ indicates a naturally occurring human mutation. The other mutations were experimental in nature.

VDRR-II indicates vitamin D-dependent rickets, type II.

The positions of the mutations seen in Table 4 in the VDR LBD in relation to the ligand $1\alpha,25(OH)_2D_3$ are shown in FIG. 6C. It is apparent that the natural [R274L, Y29Sstop, H305Q, 1314S] and the experimental [C288G] mutations, which are typified by changes in ligand binding, are all proximal to $1\alpha,25(OH)_2D_3$. In contrast the CI9ON, F244G, L254G, R391C, L417A, and E420A mutations, which do not affect ligand binding, but do display either impaired heterodimer formation or transactivation, are located at a greater distance from the $1\alpha,25(OH)_2D_3$ ligand.

F. Binding of Ligand by a Nuclear Receptor

Binding of a ligand by a nuclear receptor confers upon the receptor-ligand complex the ability to selectively interact with coactivator proteins to generate a competent transcriptional complex. Recently, site-directed scanning surface mutagenesis of the TR identified six key residues (two each on helices 3, 5, and 12) which contribute to the formation of a specific small hydrophobic cleft on the receptor surface which is essential for binding the glucocorticoid receptor-interacting protein 1 (GRIP1) or steroid receptor coactivator (SRC-1) coactivators (*Science*, 280: 1747 (1998)).

Two of the residues, one each on helices 3 and 12, are completely conserved among nuclear receptors, including the VDR [K246, E420]. Ligand activation of transcription is achieved by folding the receptor helix 12 associated with the AF-2 function against a scaffold of helices 3–6 to create a small hydrophobic cleft (~300 Å) on the surface of the receptor that is postulated to match a complementary region on the surface of the coactivator.

FIG. 6D illustrates a putative ligand-dependent GRIP1 coactivator binding site on the surface of the VDR. By analogy with the TR, the VDR coactivator binding cleft contains charged and hydrophobic residues at its periphery, but only hydrophobic residues at its center. Residues that are postulated to form the surface cleft include I238, I242, and K246 from helix 3, I260, L263, and K264 from helix 5, A267 from helix 6, and L417, E420 and V421 from helix 12.

The formation of the cleft is stabilized by a salt bridge between the two TR VDR conserved residues, E420 (helix 12) and K264 (helix 5). It is also known (Table 4) that mutation of L417A (*J. Biol. Chem.*, 272:14592 (1997)) which seems to be involved in formation of the coactivator cleft results in impairment of VDR transactivation. A key feature of the coactivator binding site is that it is formed in response to the receptor binding an agonist ligand which results in a movement of helix 12 from the 'open' portal position (FIG. 6B) to that of the 'closed' portal position of FIG. 6D. It is known that binding of ligand by the VDR does result in clearly detectable conformational changes as evaluated by differences in trypsin sensitivity according to *J. Biol. Chem.*, 270:10551 (1995).

G. Structure-Function Relationship of Ligand-VDR LBD

A structure-function relationship between the ligand and the VDR LBD relates to determination of the optimal shape(s) of the ligand which facilitates entrance through the portal of the VDR LBD (FIG. 6B) as contrasted with that required for docking of the ligand $1\alpha$-OH, $3\beta$-OH and 25-OH groups with their nominee hydrogen bond partners on the protein.

The optimal ligand shape for entrance into the VDR LBD could be a 'slim' [$1\alpha,25(OH)_2$-6-s-trans-$D_3$] molecule while the optimal shape for the ultimate docking with nominee hydrogen bond donors could be closer to the classic steroid 'pudgy' [$1\alpha,25(OH)_2$-6-s-cis-$D_3$] shaped molecule.

If there are two different optimal shapes of the ligand, this implies that there must be sufficient volume available in the LBD cavity for the conformationally flexible 1α,25(OH)$_2$D$_3$ to achieve the necessary alterations in its shape.

A description of the many shapes of 1α,25(OH)$_2$D$_3$ which arise because of the conformational flexibility of the A-ring, rotation about the 6,7 carbon single bond and the conformational mobility of the side chain are summarized in FIG. 7, described above. Because vitamin D and its daughter metabolites do not have a 9,10 carbon single bond, that is, the B-ring is broken, which is a characteristic of a seco steroid, the cyclohexane A-ring is no longer fused to the B-ring and is free to undergo chair-chair inversion between conformer A and conformer B (FIG. 7C). The principal structural change is the inversion of the 1α-OH/3β-OH pair of the cyclohexane ring from the axial/equatorial (conformer A) to the equatorial/axial (conformer B) orientation. This has the consequence of moving each hydroxyl approximately 3.8 Å, which is enough to disrupt the postulated stabilizing hydrogen bonds between the VDR LBD and ligand.

There are also significant consequences for the 1α,25 (OH)$_2$D$_3$molecule when it undergoes a 180° rotation about the 6,7 carbon single bond in, for example, 6-s-cis conformer vs. 6-s-trans conformer as seen in FIG. 7D. When the chair conformer A of a 6-s-cis 1α,25(OH)$_2$D$_3$ molecule is exactly aligned with the chair conformer A of a 6-s-trans 1α,25(OH)$_2$D$_3$ molecule, with both side chains in their global minimum position (FIG. 7B), the distance from the 1α-OH to 25-OH increases from 11.7 to 14.7 A and for the 3β-OH to 25-OH group increases from 9.6 to 14.9 A in changing from the 6-s-cis to 6-s-trans orientation. These are distance changes capable of disrupting hydrogen bonds between the ligand and VDR LBD.

There is restricted volume of the interior cavity of the VDR LBD (620 A$^3$ by analogy with TR) in relation to the volume of a 1α,25(OH)$_2$D$_3$ molecule (375 A$^3$). Therefore, there may not be sufficient room for a 1α,25(OH)$_2$D$_3$ molecule when present in the VDR LBD to carry out the necessary 180° rotation required to convert from the 6-s-cis to the 6-s-trans orientation and if so, the LBD volume may only accommodate the chair conformer A and chair conformer B cyclohexane ring interconversions (FIG. 7C).

H. Evaluation of the Ligand-VDR LBD Docking

When evaluating a seco steroid ligand for docking into the VDR LBD, careful consideration must be given to determining which of the two cyclohexane ring chair conformers (A vs. B) and which of the two orientations about the 6,7 single carbon bond (cis vs. trans) are appropriate for utilization. These four configurations can be designated as A-cis, B-cis, A-trans and B-trans, respectively. Accordingly, four case studies were identified for comparison of these four configurations. In each of these cases, the reference shape is that of the molecule in the A-cis [chair conformer A of 1α,25(OH)$_2$-6-s-cis -D$_3$] configuration. Panels E, F, G and H of FIG. 6 illustrate these four comparisons.

Case #1

In case # 1, A-cis vs. B-cis confirmation was studied. Results are seen in FIG. 6E.

Figure 6G:
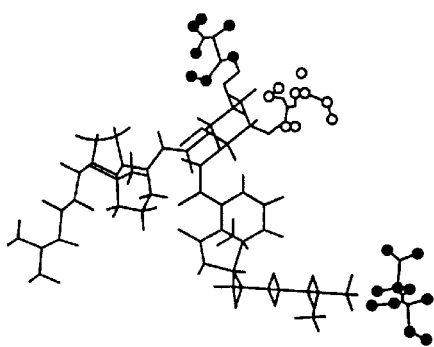
Figure 6F:
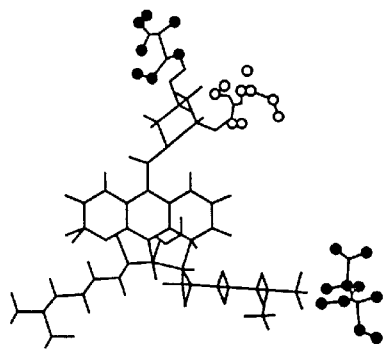
Figure 6E:
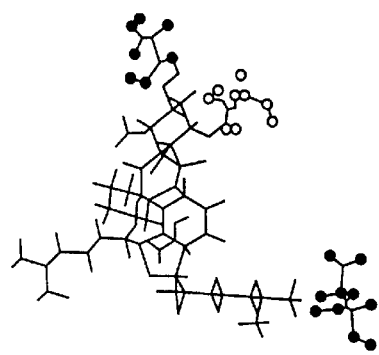

When an A-cis molecule is docked in the VDR LBD, it is apparent that the axial 1α-OH and equatorial 3β-OH groups can be readily positioned close to the VDR nominee hydrogen bond S237/S275 donor pair (FIGS. 6A and 6E). However, it is not possible to achieve the same three-dimensional relationship between the two A-ring hydroxyls and the VDR S237/S275 pair when docking a B-cis molecule because of the inversion of orientation of the two 1α-OH and 3β-OH groups to become equatorial and axial, respectively (FIG. 6C).

An appropriate relationship of the hydroxyls of B-cis with the S237/S275 donor pair can only be achieved by turning the molecule over by rotating it 180° along its long axis. This up-side-down orientation of B-cis could permit the necessary axial/equatorial orientation of the two A-ring hydroxyl groups with the S237/S275 donor pair so as to mimic that described above for the A-cis conformer (FIG. 6E).

In this up-side-down B-cis orientation, the 3β-OH is docked with 5237 and the 1α-OH with S275 which is the reverse of the docking arrangement for A-cis. Also, the 10,19 methylene groups of the A-cis and up-side-down B-cis are on opposite sides of the molecules. In addition, the C/D rings are not well aligned and the side chains are widely separated. Thus neither the B-cis nor the up-side-down B-cis orientations are likely viable ligands for the VDR.

Case #2

In case # 2, A-cis vs. A-trans confirmation was studied. Results are seen in FIG. 6F.

When the A-ring of an A-cis molecule is exactly aligned with the A-ring of an A-trans molecule as in the example when axial 1α-OH and equatorial 3β-OH groups are superimposed, it is apparent that the C/D rings of the two molecules do not align and that there is a wide separation of their side chains. This occurs because of the 180° rotation around the 6,7 bond of the A-trans in relation to the A-cis. Thus, this A-trans orientation is not a likely viable ligand for the VDR.

Case #3

In case #3, A-cis vs. up-side-down A-trans configuration was studied. Results are seen in FIG. 6G.

When an A-trans molecule is turned over by rotating it 180° around its long axis and then the A-ring is superimposed on the A-ring of a molecule in the A-cis orientation, neither the 1α-OH nor 3β-OH groups are superimposable (since both molecules are chair conformer A, but rotated 180°), nor are the C/D rings aligned. In addition, the side chains are widely separated.

Thus since the 1α-OH, 3β-OH and 25-OH groups cannot align with the VDR LBD nominee hydrogen bonds, this orientation of the A-trans orientation of 1α,25(OH)$_2$-6-s-trans-D$_3$ also is not a likely viable ligand for the VDR.

Case #4

In case #4, A-cis vs. B-trans configuration was studied. Results are seen in FIG. 3H.

When an A-cis configuration is compared with a B-trans, a surprisingly similar alignment of the two ligands can be achieved. While the two C/D rings are not superimposed, they are parallel, and displaced by only 2.4 Å, and the side chains are also approximately parallel.

Thus this conformer of 1α,25(OH)$_2$-6-s-trans-D$_3$ (B-trans) can be docked with the three nominee hydrogen bond donors for the 1α-OH, 3β-OH and 25-OH groups (S237,S275 and Y401). This orientation is likely to result in a viable ligand.

1. Biological Activities of Ligands

A test of the biological activities of ligands chemically locked in either the 6-s-cis or 6-s-trans orientation has been determined with respect to their ability to bind to the VDR and to effect transactivation in whole cell assays according to *Molecular Endocrinol.*, 11:1518 (1997).

Ligands that were locked either in the planar-s-trans [1α,25(OH)$_2$-tachysterol$_3$] or the planar-s-cis [1α,25(OH)$_2$-7-lumisterol$_3$] and do not duplicate any of the shapes seen in FIG. 6E, were both poor agonists for the VDR. Their biological activity was only 0.1–1.0% the activity of the conformationally flexible $1\alpha,25(OH)_2D_3$.

These results show that optimal shape of a ligand for the VDR LBD is one where the plane of the A-ring in relation to the C/D ring is at some intermediate angle (0–90°), as depicted by the α-conformer and β-conformer representations of FIG. 6E.

One striking ligand-receptor structure-function relationship for $1\alpha,25(OH)_2D_3$ analogs relates to the chiral center at carbon 20 (see FIG. 7A) of the steroid side chain. The 20-epi analogs are 100–10,000 times more transcriptionally potent than the natural hormone $1\alpha,25(OH)_2D_3$, even though their affinity for the VDR is not greater. It is also known that the side chain of 20-normal versus 20-epi analogs of $1\alpha,25$ $(OH)_2$ $D_3$ is able to access different regions of three-dimensional space around the C/D ring. Thus, the position of global minimum energy for the 20-normal analogs [$1\alpha,25$ $(OH)_2$ $D_3$] is oriented to the "northeast" as seen in FIG. 7B, while for 20-epi analogs it is towards the "northwest", see Bioorg. Med. Chem. Lett., 3:1799 (1998).

The seemingly benign structural change of the ligand from a 20-normal to 20-epi $1\alpha,25(OH)_2D_3$ results in a new conformational change in the VDR as assessed by trypsin sensitivity. This conformational change is believed to reflect an altered orientation of helix 12. Thus a VDR with a 20-epi ligand has an enhanced dimerization with RXR, resulting in increased transactivation of the osteocalcin promoter.

Orientation of the $1\alpha,25(OH)_2D_3$ side chain towards helix 12, rather than towards the interior of the VDR LBD, is supported by biological activity evaluation of five carboxy terminal truncation mutants of the VDR (L390/TGA, E396/TGA, C403/TGA, C410/TGA and E420/TGA). Differences in ligand potency between 20-normal and 20-epi analogs were ascribed to multiple and different contact sites of the side chains with the VDR LBD AF-2 domain (helix 12 in FIG. 7A).

The problem of docking in the VDR LBD a unique analog of $1\alpha,25(OH)_2D_3$ that has a second side chain attached to carbon 20, such as Gemini [21-(3'-hydroxy-3-methylbutyl)-$1\alpha,25(OH)_2D_3$], was also evaluated. Thus, Gemini has both a 20-normal and a 20-epi side chain. Gemini binds 40% as well as $1\alpha,25(OH)_2D_3$ to the VDR, but is 13-fold more potent than $1\alpha,25(OH)_2D_3$ with respect to transactivation of the osteocalcin promoter. The Gemini occupied VDR LBD displays a trypsin protease sensitivity different from both the 20-normal or 20-epi versions of $1\alpha,25(OH)_2D_3$ which has been interpreted to be reflective of a unique shape of the holo receptor. It shows that it is not feasible for Gemini to enter through the VDR open portal leading with its two side chains which, given their conformational flexibility, seen in FIG. 7B, create an improbably large bulk to be readily accommodated. This conclusion is also consistent both with the proposal that the ligand enters the VDR LBD leading with its A-ring and with the unique trypsin sensitivity of a VDR LBD-Gemini complex.

This protease sensitivity reflects the interaction of both Gemini side chains with helix 12 to generate a unique shape resulting in exceptional transactivation potency in comparison to when the 20-normal $1\alpha,25(OH)_2D_3$ is the ligand.

Another feature of VDR LBD is the multiplicity of proposed hydrogen bond donor/acceptors for the side chain of the ligand. These include H305, S306, Y401, S405, and T415. This is a reflection of the fact that a VDR receptor with multiple docking sites for the 25-OH of the conformationally flexible side chain of $1\alpha,25(OH)_2D_3$ has an advantage over a VDR receptor with only one docking site for the 25-OH group. It is also interesting that the natural mutation H305 of VDR has an 80% decreased ligand affinity. This suggests a functional involvement of H305 in some aspect of ligand binding.

H305 seems to be important in the open portal mode of the VDR (FIG. 7B) to stabilize the side chain under circumstances where the three other nominee hydrogen bond donors (Y401, S405, and T415) for the 25-OH group are inaccessible because helix 12 has moved to the open position. Only when helix 12 is closed are these three donors accessible to the 25-OH group.

IV. Usefulness of the Current Model

The current model has been used to describe the interactions of the conformationally flexible natural hormone, $1\alpha,25$-dihydroxy-vitamin $D_3$ [$1\alpha,25(OH)_2D_3$], and a number of related analogs with the VDR LBD. The optimal orientation of the $1\alpha,25(OH)_2D_3$ in the LBD was found to be with its A-ring directed towards the interior and its flexible side chain pointing towards and interacting with helix-12, site of the activation function-2 domain (AF-2) of the VDR. Mapping of four natural and one experimental point mutations of the VDR LBD, which result in ligand-related receptor dysfunction, indicates the close proximity of these amino acids to the bound ligand.

The present model of the VDR LBD is useful for visualizing structure-function relationships between the receptor and its natural hormone, $1\alpha,25(OH)_2D_3$, as well as a number of analogs. The potential complexity of the relationships between the VDR and the conformationally flexible ligand $1\alpha,25(OH)_2D_3$ permits rational drug design.

The model has predictive value, so that, for example, it will be possible to carry out site directed mutagenesis of the VDR LBD nominee residues for interacting with the key the $1\alpha$-OH, $3\beta$-OH and 25-OH groups. Additionally, the current VDR LBD model has facilitated analysis of the other surface domains, such as that for GRIP1, and is also anticipated to be useful for understanding the structural relationships important for heterodimer formation between the VDR and RXR.

V. A Method For Evaluation of Vitamin D Analogs as Ligands of VDR LBD

In practice, the invention requires access to a computer, such as for example, a Silicon Graphics work station that is able to work with the file of data describing the atomic coordinates for the atoms present in the α-carbon chain of residues 142–427 of the VDR-LBD. This is conveniently accomplished by using the Insight II molecular modeling program to carry out the appropriate manipulations of the data file to provide access in an operator-controlled fashion to the structural details of the three-dimensional model of the VDR LBD. At the same time, the operator "chemically synthesizes" various ligands and $1\alpha,25(OH)_2D_3$ analogs within the context of a computer file. New potential ligands for the VDR are evaluated and tested for their ability to interact with the VDR-LBD.

One possible modification of the method is to utilize a second alignment of the VDR-LBD with the primary amino acid sequence of the LBD of the thyroid receptor, as described above.

VI. The Predictive Utility of the Model

Using the three-dimensional model described herein, five groups of compounds (I–V) were designed. The structures of these compounds are seen in Tables 5–9.

A. $1\alpha,25$-Dihydroxy vitamin $D_3$ Ligands

Representative compounds of the five groups of vitamin $1\alpha,25(OH)_2D_3$ ligands were evaluated by the model according to the invention. Results were seen in Table 1. These analogs have biological activity as agonists of the slow genomic responses or agonists or antagonists of the rapid nongenomic responses.

The group I is represented by compounds having a general formula I

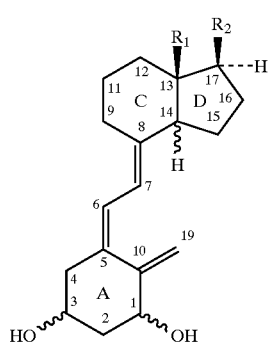

(I)

wherein C1 and C3 are configurational isomers α and β which may be the same or different in α-α, β-β, α-β or β-α configuration;
wherein C5–C6 double bond is cis or trans;
wherein C7–C8 double bond is cis or trans;
wherein C14 hydrogen is α or β;
wherein C16–C17 is a single or double bond;
wherein $R_1$ is $CH_3$ or $CH_2OH$;
wherein $R_2$ is a substituent selected from the group consisting of substituents I-1 through I-10

I-1
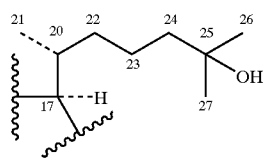

I-2
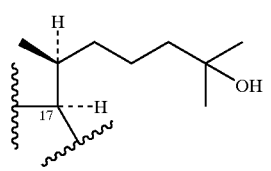

I-3
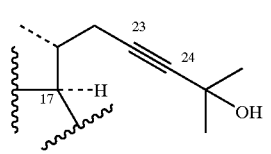

I-4
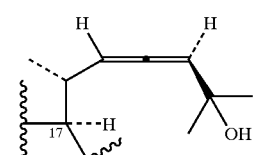

I-5
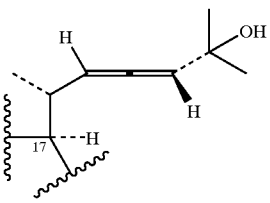

I-6
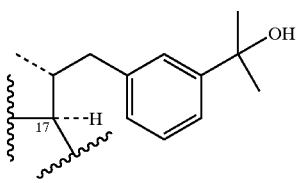

I-7
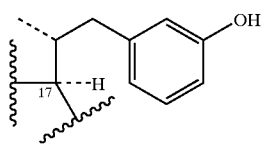

I-8
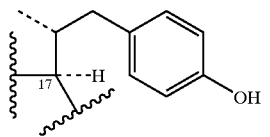

I-9
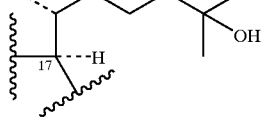

I-10
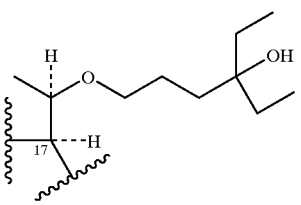

The substituents I-1–I-10 are the same as substituents II-1–II-10, III-1–III-10, IV-1–IV-10 and V-1–V-10. The designation I, II, III, IV and V show the group of the compounds having the general formula I, II, III, IV or V to which the substituent selected form the substituents 1–10 is attached as $R_1$ or $R_2$.

Table 5 lists subgroups of analogs falling within the scope of the Group I.

TABLE 5

| Formula | $C_1$–$C_3$ | $C_5$–$C_6$ | $C_7$–$C_8$ | $C_{14}$ | $C_{16}$–$C_{17}$ | $R_1$ | $R_2$ Substituents |
|---|---|---|---|---|---|---|---|
| I/1 | α-α, β-β, α-β, β-α | cis or trans | cis or trans | α or β | single double | $CH_3$ or $CH_2OH$ | all |
| I/2 | β-β | cis | trans | α | single | $CH_3$ | all |
| I/3 | β-β | cis | trans | α | single | $CH_3$ | I-2,9,10 |
| I/4 | β-β | cis | trans | α | single | $CH_3$ | analog HL |
| I/5 | α-β | cis | trans | α | single | $CH_2OH$ | all |
| I/6 | α-β | cis | trans | α | single | $CH_2OH$ | I-2,3,9,10 |
| I/7 | β-β | cis | trans | α | single | $CH_2OH$ | all |
| I/8 | β-β | H cis | trans | α | single | $CH_2O$ | I-2,3,9,10 |
| I/9 | α-β | cis | trans | β | single | $CH_3$ or $CH_2OH$ | all |
| I/10 | α-β | cis | trans | β | single | $CH_3$ or $CH_2OH$ | I,2,3,4,9,10 |
| I/11 | β-β | cis | trans | β | single | $CH_3$ or $CH_2OH$ | all |
| I/12 | β-β | cis | trans | β | single | $CH_3$ or $CH_2OH$ | I,3,4,9,10 |
| I/13 | β-β | cis | trans | α | double | $CH_3$ | all |
| I/14 | α-β | cis | trans | α | single | $CH_2OH$ | all |
| I/15 | β-β | cis | trans | α | single | $CH_2OH$ | all |
| I/16 | α-β | cis | trans | β | single | $CH_3$ or $CH_2OH$ | all |
| I/17 | β-β | cis | trans | β | single | $CH_3$ or $CH_2OH$ | all |
| I/18 | β-α | cis | trans | α | single | $CH_3$ | analog HH |
| I/19 | α-β | cis | trans | α | single | $CH_3$ | analog HJ |
| I/20 | α-β | cis | trans | α | single | $CH_2OH$ | analog HS |
| I/21 | α-β | cis | trans | β | single | $CH_3$ | analog GE |
| I/22 | α-β | cis | trans | α | single | $CH_3$ | analog DE |
| I/23 | α-β | cis | trans | α | single | $CH_3$ | analog DF |
| I/24 | α-β | cis | trans | α | single | $CH_3$ | analog HQ |
| I/25 | α-β | cis | trans | α | single | $CH_3$ | analog HR |
| I/26 | α-β | cis | trans | α | single | $CH_3$ | analog EV |
| I/27 | α-β | cis or trans | cis | α | single or double | $CH_3$ | all |
| I/28 | α-β | cis or trans | cis | α | single or double | $CH_3$ | I-1 |
| I/29 | α-β | trans | cis | α | single | $CH_3$ | analog JS |
| I/30 | α-β | cis | cis | α | single | $CH_3$ | analog JR |
| I/80 | deoxy-β | cis | trans | α | single | $CH_3$ | analog JX |
| I/81 | deoxy-β | cis | trans | α | single | CH | analog JY |
| I/84 | α-β | cis | trans | α | single | $CH_3$ | analog IB |

These analogs, depending on their structure, have a biological activity as agonists or antagonists of slow genomic responses and the rapid nongenomic responses.

The antagonists of the Group I are represented by the generic formula I wherein $R_1$ is methyl, C1 hydroxyl is in β configuration, C3 hydroxyl is in β configuration, C14 hydrogen is in α configuration and $R_2$ is the substituent 2, 9, 10.

The representative analog is the analog HL.

The agonists of Group I are represented by a general formula I wherein $R_1$ is $CH_2OH$, C1 hydroxyl is in α configuration, C3 hydroxyl is in β configuration, C14 hydrogen is in α configuration and $R_2$ are the substituents I-1–I-10, preferably substituents I-2, I-3, I-4, I-9 and I-10.

In the same group, the antagonist are compounds wherein $R_1$ is $CH_2OH$, C1 hydroxyl is in β configuration, C3 hydroxyl is in β configuration, C14 hydrogen is in α configuration and $R_2$ are the substituents I-1–I-10, preferably substituents I-2, I-3, I-9 and I-10.

The group of agonists is represented by a general formula I wherein $R_1$ is $CH_3$ or $CH_2OH$, C1 hydroxyl is in α configuration, C3 hydroxyl is in β configuration, C14 hydrogen is in β configuration and $R_2$ are the substituents I-1–I-10, preferably substituents I-1, I-2, I-3, I-4, I-9 and I-10.

The group of antagonists is represented by a general formula I wherein $R_1$ is $CH_3$ or $CH_2OH$, C1 hydroxyl is in β configuration, C3 hydroxyl is in β configuration, C14 hydrogen is in β configuration and $R_2$ are the substituents I-1–I-10, preferably substituents I-1, I-2, I-3, I-4, I-9 and I-10.

The group II is represented by compounds having a general formula II

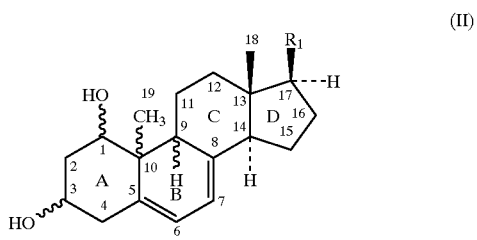

(II)

wherein C1 and C3 are positional isomers α and β which may be the same or different in α-α, β-β, α-β or β-α configuration;

wherein C9 hydrogen and C10 methyl are positional isomers α and β which may be the same or different in α-α, β-β, α-β or β-α configuration;

wherein C16–C17 is a single or double bond;

wherein $R_1$ is a substituent selected from the group consisting of substituents II-1 through II-10

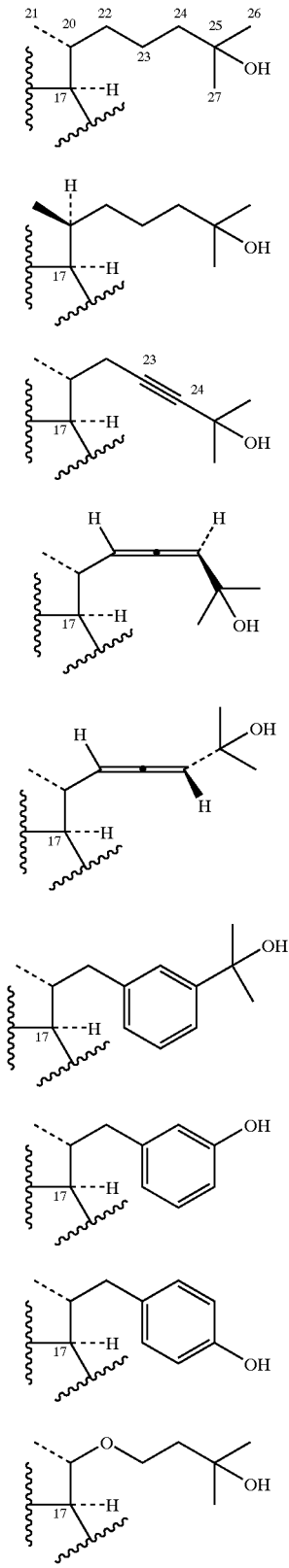

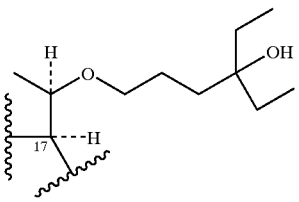

Table 6 lists subgroups of analogs falling within the scope of the Group II.

TABLE 6

| Formula | C1–C3 | C9H–C10CH3 | C16–C17 | $R_1$ Substituents |
|---|---|---|---|---|
| II/31 | α-α, β-β, α-β, β-α | αα, αβ, ββ, βα | single double | all |
| II/32 | β-β | β-α | single double | all |
| II/33 | β-β | β-α | single double | II-1,2,4,10 |
| II/34 | β-β | α-β | single double | all |
| II/35 | β-β | α-β | single double | II-1,2,4,10 |
| II/36 | α-β | α-α | single double | all |
| II/37 | α-β | α-α | single double | II-1,2,4,10 |
| II/38 | α-β | α-α | single | analog JO Check (II-I) |
| II/39 | α-β | β-α | single double | all |
| II/40 | α-β | β-α | single | II-1,2,4,10 |
| II/41 | α-β | β-α | single | analog JN (II-1) |
| II/42 | α-β | β-β | single double | all |
| II/43 | α-β | β-β | single double | II-1,2,4,10 |
| II/44 | α-β | β-β | single | analog Jp (II-1) |
| II/45 | α-β | β-α | single double | all |
| II/46 | α-β | β-α | single double | II-1,2,4,10 |
| II/47 | α-β | β-α | single | analog JM (II-1) |
| II/48 | α-α | β-α | single double | II-1,2,4,10 |
| II/49 | α-α | α-β | single double | II-1,2,4,10 |
| II/50 | β-α | β-α | single double | II-1,2,4,10 |

The analogs listed in Group II are represented by the analogs identified as JM, JN, JO and JP. These analogs, depending on their structure are conformationally restricted and are not good candidates as VRD LBD ligands.

In Group II, the antagonists are represented by the generic formula II wherein C1 hydroxyl is in β configuration, C3 hydroxyl is in β configuration, C9 hydrogen is in β and C10 methyl is in α configuration and $R_1$ is the substituent II-1, II-2, II-4 and II-10, preferably the substituents II-1, II-2, and II-10, or wherein C1 hydrogen is in β and C3 is in β configuration, C9 hydrogen is in α and C10 methyl is in β configuration and $R_1$ is the substituent II-1, II-2, II-7, II-10, and is preferably the substituent II-1, II-2 or II-10.

In Group II, the agonists are represented by the generic formula II wherein C1 hydroxyl is in α configuration, C3 hydroxyl is in β configuration, C9 hydrogen is in α and C10 methyl is in α configuration and $R_1$ is the substituent II-1, II-2, II-4, II-10, and preferably it is the substituent II-1, II-2, and II-13. The specific agonist of this group is the analog JO where $R_1$ is the substituent II-1.

The other agonists of the Group II are represented by the general formula II wherein C1 hydroxyl is in α and C3 hydroxyl is in β configuration, C9 hydrogen is in β and C10 methyl is in α configuration and $R_1$ is the substituent II-1, II-2, II-4, II-10 and, preferably, it is the substituent II-1, II-2 and II-10. The specific agonist of this group is the analog JN where $R_1$ is the substituent II-1.

The other agonists of the Group II are represented by the general formula II wherein C1 hydroxyl is in α and C3 hydroxyl is in β configuration, C9 hydrogen is in β and C10 methyl is in α configuration and $R_1$ is the substituent II-1–II-10, preferably the substituent II-1, II-2, II-4 and II-10. The specific agonist of this group is the analog JM where $R_1$ is the substituent II-1.

Still another agonists of the Group II are represented by the general formula II wherein C1 hydroxyl is in α and C3 hydroxyl is in β configuration, C9 hydrogen is in β and C10 methyl is in β configuration and $R_1$ is the substituent II-1–II-10, preferably II-1, II-2, II-4 and II-10. The specific agonist of this group is the analog JP where $R_1$ is the substituent II-1.

The group III is represented by compounds having a general formula III

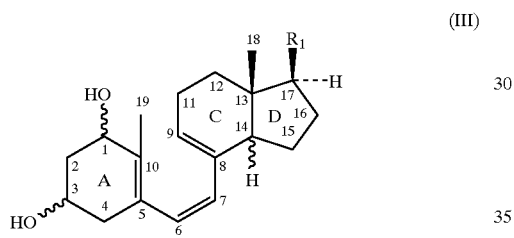
(III)

wherein C1 and C3 are positional isomers α and β which may be the same or different in α-α, β-β, α-β or β-α configuration;

wherein C14 hydrogen is α or β;

wherein C16–C17 is a single or double bond;

wherein $R_1$ is a substituent selected from the group consisting of substituents III-1 through III-10

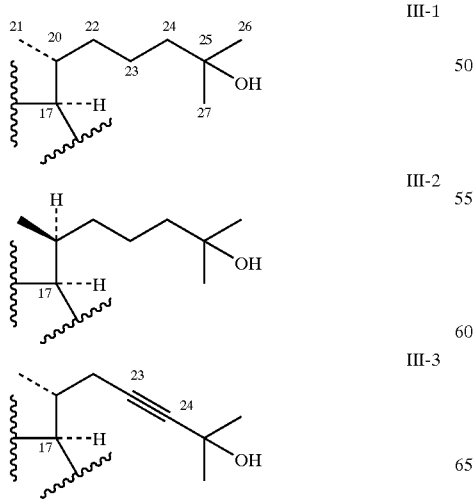

III-1

III-2

III-3

-continued

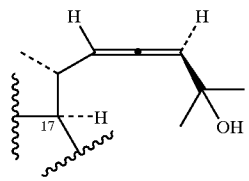
III-4

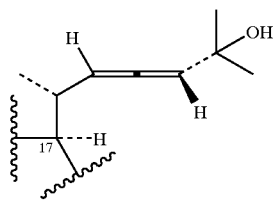
III-5

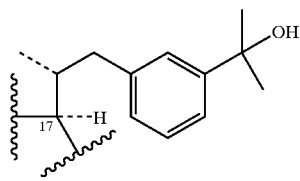
III-6

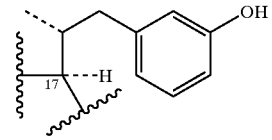
III-7

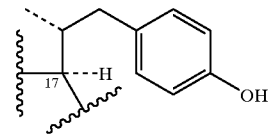
III-8

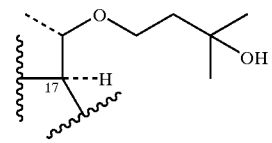
III-9

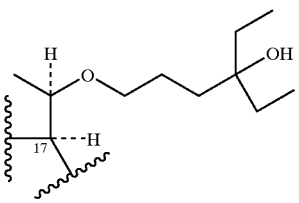
III-10

Table 7 lists subgroups of analogs falling within the scope of the Group III.

TABLE 7

| Formula | C1–C5 | C14 | C16–C17 | $R_1$ Substituents |
|---|---|---|---|---|
| III/51 | αα, αβ, βα, ββ | α or β | single double | all |
| III/52 | β-β | α | single double | all |
| III/53 | β-β | α | single double | III-1,2,4,7,9,10 |
| III/54 | α-β | α | single double | all |
| III/55 | α-β | α | single double | III-1,2,4,7,9,10 |

TABLE 7-continued

| Formula | C1–C5 | C14 | C16–C17 | $R_1$ Substituents |
|---|---|---|---|---|
| III/56 | β-β | β | single double | all |
| III/57 | β-β | β | single double | III-1,2,4,7,9,10 |
| III/58 | α-β | β | single double | all |
| III/59 | α-β | β | single double | III-1,2,4,7,9,10 |
| III/60 | α-β | β | single | analog GF (III-1) |

The analogs listed in Group III are represented by the analog identified as GF. These analogs of Group III, depending on their structure and configuration, have a biological activity as agonists or antagonists of slow genomic responses and agonists or antagonists of the rapid nongenomic responses.

In Group III, the agonists and antagonists are represented by the generic formula III wherein C1 hydroxyl is in α or β configuration, C3 hydroxyl is in β configuration, C14 hydrogen is in α or β configuration, C16–C17 is a single or double bond and $R_1$ is the substituent III-1–III-10.

Preferred group of compounds of the Group III are compounds wherein C1 is in α configuration, C3 is in β configuration and the $R_1$ substituent is selected from the group III-1–III-10.

The specific agonist of this group is the analog GF where $R_1$ is the substituent III-1.

The group IV is represented by compounds having a general formula IV

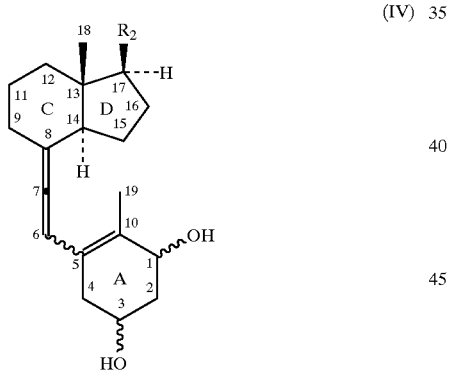

(IV)

wherein C1 and C3 hydroxyls are positional isomers α and β which may be the same or different in α-α, β-β, α-β or β-α configuration;
wherein the C5–C6 is in α or β configuration;
wherein C14 hydrogen is α;
wherein C16–C17 is a single or double bond;
wherein $R_1$ is a substituent selected from the group consisting of substituents IV-1 through IV-10

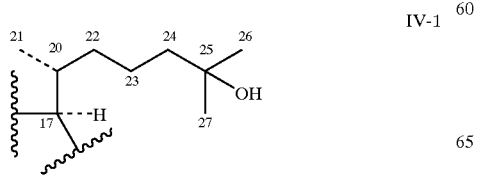

IV-1

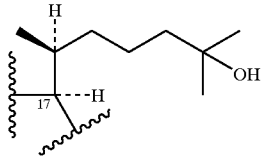

IV-2

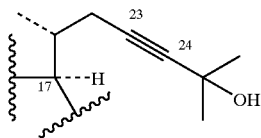

IV-3

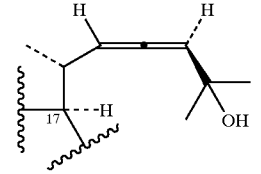

IV-4

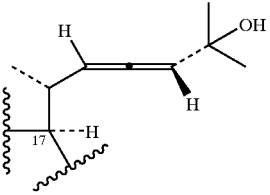

IV-5

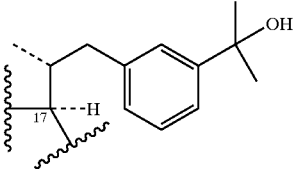

IV-6

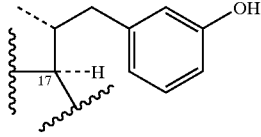

IV-7

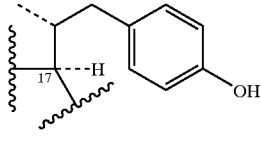

IV-8

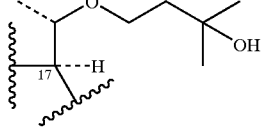

IV-9

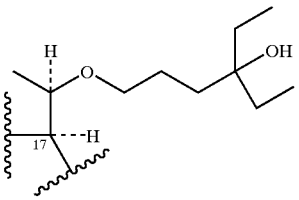

IV-10

Table 8 lists subgroups of analogs falling within the scope of the Group IV.

TABLE 8

| Formula | C1–C3 | C5–C6 | C16–C17 | $R_1$ |
|---|---|---|---|---|
| IV/61 | αα-ββ<br>αβ-ββ | α or β | single<br>double | all |
| IV/62 | α-α | α | single<br>double | all |
| IV/63 | α-α | α | single<br>double | IV-1,2,4,7,9,10 |
| IV/64 | β-β | α | single<br>double | all |
| IV/65 | β-β | α | single<br>double | IV-1,2,4,7,9,10 |
| IV/66 | α-β | α | single<br>double | all |
| IV/67 | α-β | α | single<br>double | IV-1,2,4,7,9,10 |
| IV/68 | α-β | α | single | analog JW (IV-1) |
| IV/69 | β-α | α | single<br>double | all |
| IV/70 | β-β | α | single<br>double | IV-1,2,4,7,9,10 |
| IV/71 | α-α | β | single<br>double | all |
| IV/72 | α-α | β | single<br>double | IV-1,2,4,7,9,10 |
| IV/73 | β-β | β | single<br>double | all |
| IV/74 | β-β | β | single<br>double | IV-1,2,4,7,9,10 |
| IV/75 | α-β | β | single<br>double | all |
| IV/76 | α-β | β | single<br>double | IV-1,2,4,7,9,10 |
| IV/77 | α-β | β | single | analog JV (IV-1) |
| IV/78 | β-α | β | single<br>double | all |
| IV/79 | β-α | α | single<br>double | IV-1,2,4,7,9,10 |

The analogs listed in Group IV are represented by the analogs identified as analogs JV and JW. These analogs, depending on their structure and configuration, have a biological activity as agonists of slow genomic responses or as agonists or antagonists of the rapid nongenomic responses.

In Group IV, the agonists and antagonists are represented by the generic formula IV wherein C1 hydrogen is in α or β configuration, and C3 is in α or β configuration, C5–C6 is in α or β configuration, C14 hydrogen is α, C16–C17 is a single or double bond and $R_1$ is a substituent selected from the group consisting of substituents IV-1 through IV-10. Preferred agonists in this group of compounds of this group are compounds wherein C1 is in α configuration, C3 is in β configuration and the $R^1$ substituent is IV-1. The specific agonists of this group are the analogs JV and JW.

The compounds of Group V are represented by a general formula V

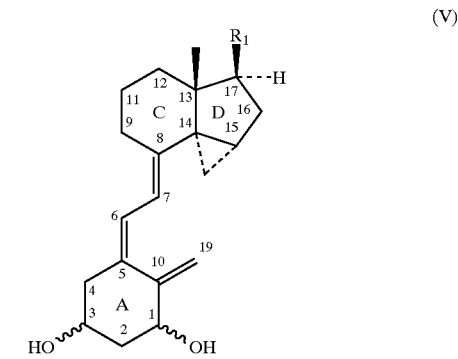

(V)

wherein C1 and C3 are positional isomers α and β which may be the same or different in αα, ββ, αβ or βα configuration,
wherein C5–C6 double band is cis and C7C8 double band is trans;
wherein C16–C17 is a single or double bond; and
wherein $R_1$ is a substituent is selected from the group consisting of substituents V-1 through V-10.

Table 9 lists subgroups of analogs falling within the scope of Group V.

TABLE 9

| Formula | C1–C3 | $R_1$ |
|---|---|---|
| V/82 | αα-ββ<br>αβ-βα | all |
| V/ | α-α | all |
| V/ | α-β | all |
| V/83 | α-β | analog LO (V-1) |
| V | β-α | all |
| V | β-β | all |

A representative analog of this group is analog LO which is an agonist of slow genomic and rapid nongenomic responses.

UTILITY

The current invention describes for the first time the development of a three-dimensional model of the ligand-binding domain of the nuclear vitamin $D_3$ receptor for the steroid hormone $1\alpha,25(OH)_2D_3$. Accordingly, this invention provides for the first time, a detailed description (within the confines of a computer modeling environment) of the interactions of proposed new analogs of $1\alpha,25(OH)_2D_3$ with the interior surface of the VDR-LBD.

The present model of VDR-LBD is useful for visualizing structure-function relationships between its receptor and its natural hormone $1\alpha,25(OH)_2D_3$ as well as a number of ligand analogs. The model has predictive value. For example, it will be possible to carry out site-directed mutagenesis of the VDR LBD nominee residues for interacting with the key $1\alpha,25$-OH, 313-OH and 25-OH groups. The potential complexity of the relationship between the VDR and the conformationally flexible ligand $1\alpha,25(OH)_2D_3$ is particularly important for rational drug design.

EXAMPLE 1

The Model of LBD of the 1α,25-Dihydroxyvitamin D3 Nuclear Receptor

The model of the LBD of the nuclear receptor for $1\alpha,25(OH)_2D_3$ was generated using the Insight II molecular modeling program (version 6.0) For the human VDR LBD, residues 142–427 were manually aligned with residues 157–410 of the rat α1 isoform of the TR. After the optimal alignment was determined, the atomic coordinates of TR, obtained from its 2.0 Å x-ray crystallographic structure according to *Nature*, 378: 690, (1995), were applied to the aligned VDR residues. The resulting model of the VDR LBD (without ligand) was then conservatively adjusted by energy minimization to a root mean square (RMS) of 0.21. This allowed the model to be subjected to 20,000 iterations of dynamics (3000K) to define the working VDR LBD model. Subsequently $1\alpha,25(OH)_2D_3$ was docked in the VDR LBD and an additional 15,000 iterations of dynamics (3000K) were run.

What is claimed:

1. A method for identification, design and selection of computer generated representations of an agonist or antagonist analog of 1α,25(OH)₂-vitamin-D₃ which binds to a nuclear receptor for 1α,25(OH)₂-vitamin-D₃, said method comprising steps:

(a) preparing a three-dimensional computer model of a ligand binding domain of a 1α,25(OH)₂-vitamin-D₃ receptor, said ligand binding domain model defined by the atomic coordinates for the atoms present in the α-carbon chain of amino acid residues 142–427 of the 1α,25(OH)₂-vitamin-D₃ ligand binding domain, said amino acid residues comprised of 12-α-helical elements linked by connecting loops;

(b) designing a three-dimensional computer model using atomic coordinates of a chemical structure of the 1α,25(OH)₂-vitamin-D₃ analog wherein said model represents a chemical structure which binds to said α-carbon chain of amino acid residues 142–427 of the 1α,25(OH)₂-vitamin-D₃ ligand binding domain;

(c) graphically representing a structure-function relationship of the three-dimensional model of the 1α,25(OH)₂-vitamin-D₃ analog with the three-dimensional computer model of the 1α,25(OH)₂-vitamin-D₃ ligand binding domain;

(d) determining a binding interaction of said analog to said receptor binding domain by detecting a number of points of contact between the model of the chemical structure of the 1α,25(OH)₂-vitamin-D₃ analog and the ligand binding domain of the inner cavity of the vitamin D₃ nuclear receptor depicted by the three-dimensional computer model of a ligand binding domain of a 1α,25(OH)₂-vitamin-D₃ receptor;

(e) evaluating the binding interaction of said analog to the ligand binding domain wherein the same or a larger number of points of contact between the analog and receptor ligand binding domain than the number of points of contact between $1\alpha,25(OH)_2$-vitamin-$D_3$ and the $1\alpha,25(OH)_2$-vitamin-$D_3$ nuclear receptor ligand binding domain indicates an analog of $1\alpha,25(OH)_2$-vitamin-$D_3$ which has the same or better biological activity as the $1\alpha,25(OH)_2$-vitamin-$D_3$ or another analog with a lower number of points of contact;

(f) identifying said analog having the same or higher number of points of contact as the $1\alpha,25(OH)_2$-vitamin-$D_3$; and (g) generating a computer representation of a chemical structure of the $1\alpha,25(OH)_2$-vitamin-$D_3$ analog which binds to said α-carbon chain of amino acid residues 142–427 of the $1\alpha,25(OH)_2$-vitamin-$D_3$ ligand binding domain $1\alpha,25(OH)_2$-vitamin-$D_3$ nuclear receptor ligand binding domain designed in step (b), evaluated in step (g), and identified in step (h).

2. The method of claim 1 wherein the analog inherently possesses or can assume a shape or conformation comparable to that of $1\alpha,25(OH)_2$-vitamin-$D_3$ bound in the interior of the ligand binding cavity in said three-dimensional model, wherein an A-ring conformer of the analog is a β-chair wherein 1α-hydroxy is equatorial and 3β-hydroxy is axial and the C6–C7 bond is +30° from a 6-s-trans orientation, or wherein the A-ring conformer is an α-chair wherein 1α-hydroxy is axial and 3β-hydroxy is equatorial and the C6–C7 bond is +30° from a 6-s-cis orientation.

3. The method of claim 1 wherein the analog is conformationally restricted to a shape assumed by $1\alpha-25(OH)_2$-vitamin-$D_3$ bound in the interior of the ligand binding cavity in said three-dimensional model, wherein an A-ring conformer of the analog is a β-chair wherein 1α-hydroxy is equatorial and 3β-hydroxy is axial and the C6–C7 bond is +30° from a 6-s-trans orientation, or wherein the A-ring conformer is an α-chair wherein 1α-hydroxy is axial and 3β-hydroxy is equatorial and the C6–C7 bond is +30° from a 6-s-cis orientation.

4. The method of claim 1 wherein the biological activity is defined as an activation of gene transcription for agonists or an inhibition of gene transcription for antagonists.

5. The method of claim 1 wherein the ligand binding domain amino acid residues 142–427 comprises a loop of either about twenty five or about forty five residues.

6. The method of claim 5 wherein the loop of about twenty five residues begins with serine 199 and ends with glutamine 223 or where the loop of about forty five residues begins at valine 159 and ends at leucine 205.

7. The method of claim 6 wherein the analog binds to the amino acid residues 142–427 of the vitamin-$D_3$ ligand binding domain within the helical elements.

8. The method of claim 7 wherein the analog is docked within the inner cavity of the ligand binding domain of the vitamin-$D_3$ nuclear receptor in such a way that 1α-hydroxy is in hydrogen bond proximity to serine 237, 3β-hydroxy is in hydrogen bond proximity to either serine 275 or serine 278 and 25-hydroxy is in hydrogen bond proximity to either histidine-305, histidine-397, tyrosine-401 or threonine-415.

9. A method for identification, design and selection of computer generated representations of an agonist or antagonist analog of $1\alpha,25(OH)_2$-vitamin-$D_3$ which binds to a nuclear receptor for $1\alpha,25(OH)_2$-vitamin-$D_3$, said method comprising steps:

(a) preparing a three-dimensional computer model of a ligand binding domain of a $1\alpha,25(OH)_2$-vitamin-$D_3$ receptor, said ligand binding domain model defined by the atomic coordinates for the atoms present in the α-carbon chain of amino acid residues 142–427 of the $1\alpha,25(OH)_2$-vitamin-$D_3$ ligand binding domain, said amino acid residues comprised of 12-α-helical elements linked by connecting loops;

(b) designing a three-dimensional model of a chemical structure of the $1\alpha,25(OH)_2$-vitamin-$D_3$ analog wherein said model represents a chemical structure which binds to said α-carbon chain of amino acid residues 142–427 of the $1\alpha,25(OH)_2$-vitamin-$D_3$ ligand binding domain;

(c) determining atomic coordinates of said analog of step (b) for the atoms present in the α-carbon chain of amino acid residues 142–427 of the $1\alpha,25(OH)_2$-vitamin-$D_3$ ligand binding domain which bind to or dock within said ligand binding domain of the receptor;

(d) entering said coordinates of said analog of step (b) within the three dimensional computer model of the ligand binding domain of $1\alpha,25(OH)_2$-vitamin $D_3$ and graphically representing a structure-function relationship of the chemical structure of the $1\alpha,25(OH)_2$-vitamin-$D_3$ analog within the three-dimensional computer model of the $1\alpha,25(OH)_2$-vitamin-$D_3$;

(e) determining a binding interaction of said analog to said receptor binding domain by detecting a number of points of contact between the model of the chemical structure of the $1\alpha,25(OH)_2$-vitamin-$D_3$ analog and the ligand binding domain of the inner cavity of the vitamin $D_3$ nuclear receptor depicted by the three-dimensional computer model of a ligand binding domain of a $1\alpha,25(OH)_2$-vitamin-$D_3$ receptor;

(f) evaluating the binding interaction of said analog to the ligand binding domain wherein the same or a larger number of points of contact between the analog and receptor ligand binding domain than the number of points of contact between, $1\alpha,25(OH)_2$-vitamin-$D_3$ and the $1\alpha,25(OH)_2$-vitamin-$D_3$ nuclear receptor ligand binding domain indicates an analog of $1\alpha,25(OH)_2$-vitamin-$D_3$ which has the same or better biological activity as the $1\alpha,25(OH)_2$-vitamin-$D_3$ or other analog with a lower number of points of contact;

(g) identifying said analog having a higher number of points of contact between $1\alpha,25(OH)_2$-vitamin-$D_3$ and the $1\alpha,25(OH)_2$-vitamin-$D_3$ nuclear receptor ligand binding domain; and (h) generating a computer representation of a chemical structure of the $1\alpha,25(OH)_2$-vitamin-$D_3$ analog α-carbon chain of amino acid residues 142–427 of the $1\alpha,25(OH)_2$-vitamin-$D_3$ ligand binding domain designed in step (b) evaluated in step (f) and identified in step (g);

wherein the biological activity is defined as an activation of gene transcription for agonists or an inhibition of gene transcription for antagonists;

wherein the ligand binding domain amino acid residues 142–427 comprises a loop of either about twenty five or about forty five residues;

wherein the loop of about twenty five residues begins with serine 199 and ends with glutamine 223 or where the loop of about forty five residues begins at valine 159 and ends at leucine 205;

wherein the analog inherently possesses or can assume a shape comparable to that of $1\alpha,25(OH)_2$-vitamin-$D_3$ bound in the interior of the ligand binding cavity in said three-dimensional model, wherein an A-ring conformer is a β-chair wherein 1α-hydroxy is equatorial and 3β-hydroxy is axial and the C6–C7 bond is +30° from a 6-s-trans orientation, or wherein the A-ring conformer is an α-chair wherein 1α-hydroxy is axial and 3β-hydroxy is equatorial and the C6–C7 bond is +30° from a 6-s-cis orientation.

10. The method of claim 9 wherein the analog is conformationally restricted to a shape assumed by 1α-25(OH)$_2$-vitamin-D$_3$ bound in the interior of the ligand binding cavity in said three-dimensional model, wherein an A-ring conformer is a β-chair wherein the 1α-hydroxy is equatorial and 3β-hydroxy is axial and the C6–C7 bond is +30° from a 6-s-trans orientation, or wherein an A-ring conformer is an α-chair wherein the 1α-hydroxy is axial and 3β-hydroxy is equatorial and the C6–C7 bond is +30° from a 6-s-cis orientation.

* * * * *

SEQUENCE LISTING

<160> NUMBER OF SEQ ID NOS: 2

<210> SEQ ID NO 1
<211> LENGTH: 287
<212> TYPE: PRT
<213> ORGANISM: Homo sapiens
<220> FEATURE:
<223> OTHER INFORMATION: Vitamin D receptor ligand binding domain

<400> SEQUENCE: 1

```
His Lys Thr Tyr Asp Pro Thr Tyr Ser Asp Phe Cys Gln Phe Arg Pro
 1               5                  10                  15

Pro Val Arg Val Asn Asp Gly Gly Ser His Pro Ser Arg Pro Asn
             20                  25                  30

Ser Arg His Thr Pro Ser Phe Ser Gly Asp Ser Ser Ser Cys Ser
         35                  40                  45

Asp His Cys Ile Thr Ser Ser Asp Met Met Asp Ser Ser Ser Phe Ser
     50                  55                  60

Asn Leu Asp Leu Ser Glu Glu Asp Ser Asp Pro Ser Val Thr Leu
65                  70                  75                  80

Glu Leu Ser Gln Leu Ser Met Leu Pro His Leu Ala Asp Leu Val Ser
                 85                  90                  95

Tyr Ser Ile Gln Lys Val Ile Gly Phe Ala Lys Met Ile Pro Gly Phe
                100                 105                 110

Arg Asp Leu Thr Ser Glu Asp Gln Ile Val Leu Leu Lys Ser Ser Ala
            115                 120                 125

Ile Glu Val Ile Met Leu Arg Ser Asn Glu Ser Phe Thr Met Asp Asp
        130                 135                 140

Met Ser Thr Cys Gly Asn Gln Asp Tyr Lys Tyr Arg Val Ser Asp Val
145                 150                 155                 160

Thr Lys Ala Gly His Ser Leu Glu Leu Ile Glu Pro Leu Ile Lys Phe
                165                 170                 175

Gln Val Gly Leu Lys Lys Leu Asn Leu His Glu Glu Glu His Val Leu
            180                 185                 190

Leu Met Ala Ile Cys Ile Val Ser Pro Asp Arg Pro Gly Val Gln Asp
        195                 200                 205

Ala Ala Leu Ile Glu Ala Ile Gln Asp Arg Leu Ser Asn Thr Leu Gln
    210                 215                 220

Thr Tyr Ile Arg Cys Arg His Pro Pro Gly Ser His Leu Leu Tyr
225                 230                 235                 240

Ala Lys Met Ile Gln Lys Leu Ala Asp Leu Arg Ser Leu Asn Glu Glu
                245                 250                 255

His Ser Lys Gln Tyr Arg Cys Leu Ser Phe Gln Pro Glu Cys Ser Met
            260                 265                 270

Lys Leu Thr Pro Leu Val Leu Glu Val Phe Gly Asn Glu Ile Ser
        275                 280                 285
```

-continued

```
<210> SEQ ID NO 2
<211> LENGTH: 251
<212> TYPE: PRT
<213> ORGANISM: Homo sapiens
<220> FEATURE:
<223> OTHER INFORMATION: Thyroid receptor ligand binding domain

<400> SEQUENCE: 2

Arg Pro Glu Pro Thr Pro Glu Glu Asp Leu Ile His Val Ala Thr Glu
  1               5                  10                  15

Ala His Arg Ser Thr Asn Ala Gln Gly Ser His Lys Gln Arg Arg Lys
             20                  25                  30

Phe Leu Pro Asp Asp Ile Gly Gln Ser Pro Ile Val Ser Met Pro Gly
         35                  40                  45

Asp Asp Lys Val Asp Leu Glu Ala Phe Ser Glu Phe Thr Lys Ile Ile
     50                  55                  60

Thr Pro Ala Ile Thr Arg Val Val Asp Phe Ala Lys Lys Leu Pro Met
 65                  70                  75                  80

Phe Ser Glu Leu Pro Cys Glu Asp Gln Ile Ile Leu Leu Lys Gly Cys
                 85                  90                  95

Cys Met Glu Ile Met Ser Leu Arg Ala Ala Val Arg Tyr Asp Pro Ala
                100                 105                 110

Ser Asp Thr Leu Thr Leu Ser Gly Glu Met Ala Val Lys Arg Glu Gln
            115                 120                 125

Leu Lys Asn Gly Gly Leu Gly Val Val Ser Asp Ala Ile Phe Glu Leu
        130                 135                 140

Gly Lys Ser Leu Ser Ala Phe Asn Leu Asp Asp Thr Glu Val Ala Leu
145                 150                 155                 160

Leu Gln Ala Val Leu Leu Met Ser Thr Asp Arg Ser Gly Leu Leu Cys
                165                 170                 175

Val Asp Ala Ile Glu Lys Ser Gln Glu Ala Tyr Leu Leu Ala Phe Glu
            180                 185                 190

His Tyr Val Asn His Arg Lys His Asn Ile Pro His Phe Pro Lys Leu
        195                 200                 205

Leu Met Lys Val Thr Asp Leu Arg Met Ile Gly Ala Cys His Ala Ser
    210                 215                 220

Arg Phe Leu His Met Lys Val Glu Cys Pro Thr Glu Leu Phe Pro Pro
225                 230                 235                 240

Leu Phe Leu Glu Val Phe Glu Asp Gln Glu Val
                245                 250
```